US010095688B1

(12) United States Patent
Schilling et al.

(10) Patent No.: US 10,095,688 B1
(45) Date of Patent: Oct. 9, 2018

(54) ADAPTIVE NETWORK QUERYING SYSTEM

(71) Applicants: Josh Schilling, Newberg, OR (US);
Praduman Jain, Fairfax, VA (US);
Dave Klein, Oakton, VA (US)

(72) Inventors: Josh Schilling, Newberg, OR (US);
Praduman Jain, Fairfax, VA (US);
Dave Klein, Oakton, VA (US)

(*) Notice: Subject to any disclaimer, the term of this patent is extended or adjusted under 35 U.S.C. 154(b) by 0 days.

(21) Appl. No.: 15/943,309

(22) Filed: Apr. 2, 2018

(51) Int. Cl.
*G06F 17/00* (2006.01)
*G06F 17/27* (2006.01)
*G06F 11/34* (2006.01)
*G09B 7/06* (2006.01)
*G06F 17/30* (2006.01)
*A61B 5/16* (2006.01)

(52) U.S. Cl.
CPC ........ *G06F 17/279* (2013.01); *G06F 11/3438* (2013.01); *G06F 17/30424* (2013.01); *G09B 7/06* (2013.01); *A61B 5/165* (2013.01)

(58) Field of Classification Search
CPC ......... G06F 17/30554; G06F 17/30864; G06F 17/30867; G06F 3/0482; G06F 17/2785
See application file for complete search history.

(56) References Cited

U.S. PATENT DOCUMENTS

| | | | |
|---|---|---|---|
| 9,201,979 B2 | 12/2015 | Ramer | |
| 9,449,336 B2 | 9/2016 | Wilson et al. | |
| 9,519,772 B2 | 12/2016 | Harrison | |
| 9,760,910 B1 | 9/2017 | Tuchman et al. | |
| 2008/0249857 A1 | 10/2008 | Angell | |

*Primary Examiner* — Truong Vo
(74) *Attorney, Agent, or Firm* — Attentive Law; Paul Ratcliffe

(57) ABSTRACT

The systems and methods of the invention provide a network querying or content system which drives high relevance question sets or content to users and presents it in the optimal template to ensure user interaction. In accord with at least one aspect, the system assesses the context (of a user) by interpreting the optimal template based on personality mapping of the user and relevancy mapping of the query or content. In a technically efficient manner, the system employs client-based managers and builders to select, supplement, or build user profiles and user interface templates to optimize queries or content based on a user's present profile. The systems and methods of the invention perform processing, in a technically efficient manner, to assess question or content set interaction and relevancy to generate targeted question sets or content that encourage overall user health and wellness.

24 Claims, 13 Drawing Sheets

ADAPTIVE NETWORK QUERYING SYSTEM

FIELD OF THE INVENTION

This present invention relates to the field of adaptive networks and more specifically to adaptive network systems for smart querying of users.

BACKGROUND OF THE INVENTION

Current technological environments, various services, user device applications and other platforms send queries or surveys to users based on the goals of the questioner and/or in some predetermined scheduled style or manner, for example.

These current query systems are designed to send questions to users uncertain if the user will see, interact with, or answer any of the queries. However, this leads to inefficiencies as queries are often sent without interaction, sent multiple times, and often with little response or questionable accuracy and relevancy. The current inefficient systems not only clog networks with multiple and redundant queries, they also clog the user's equipment such as mobile phones, docking systems like in-dash vehicle displays, voice activated equipment, laptops and smart watches; consume excessive power of the user's varying equipment and the network, consume bandwidth, and make the user disinterested in further queries. These inefficiencies cost both the provider and user.

Therefore, technical improvements and solutions are needed to overcome these technical problems while accommodating the evolving needs of users. The systems and methods of the present invention provide such improvements.

SUMMARY OF INVENTION

The present invention provides a network querying system and method which drives high relevance question sets to users and presents it in the optimal template to maximize user interaction. The system assesses the context (of a user) by interpreting the optimal template based on personality mapping of the user and relevancy mapping of the query or content. The system employs client-based managers and builders to select, supplement, or build user profiles and user interface templates to optimize queries based on a user's present profile in a technically efficient manner. The systems and methods of the invention perform processing, in a technically efficient manner, to assess question set interaction and relevancy to generate targeted question sets that encourage overall user health and wellness.

The present invention also provides a system of networked apparatuses that provide adaptive queries, with the processing being performed over a network which provides a communication interface amongst the networked apparatuses, each of the apparatuses in the form of a tangibly embodied computer processor, each computer processor including instructions on a non-transitory computer memory. The system comprised of: the network over which a plurality of networked apparatuses communicate; an adaptive query server, the adaptive query server including: a query processor including instructions on a non-transitory computer medium, the non-transitory computer medium constituted by one or more data storage mediums; the query processor including a training manager module for loading at least one query; the query processor including a personality mapping module for mapping at least one recipient profile to create a recipient profile file for each individual recipient associated with the plurality of networked apparatuses, the recipient profile file stored in the one or more data storage mediums; the query processor including a relevancy mapping module for mapping the relevancy of the one or more queries to a plurality of individual recipients associated with the plurality of networked apparatuses; the query processor determining a query for a selected recipient based on the recipient profile file associated with the recipient and the relevancy mapping of the query; the query processor generating a query message including data on the query, the selected recipient profile, and a suggested recipient interface template; and the query processor initiating a communication including the query message to at least one recipient device associated with the selected recipient. The system further including at least one recipient device, with the recipient device including: an adaptive processor including instructions on a non-transitory computer medium, the non-transitory computer medium constituted by one of more data storage mediums; the adaptive processor including a profile module for determining a real time profile of the recipient associated with the recipient device and storing the profile in one of the data storage mediums on the device; the adaptive processor processing the query message to extract the query, the selected recipient profile, and the suggested recipient interface template; the adaptive processor comparing the selected recipient profile from the adaptive query server to the profile file on the recipient device; the adaptive processor including a profile manager and selecting a final recipient profile from a plurality of recipient profiles stored in the one or more data storage mediums based on the comparison; the adaptive processor including a user interface manager, the user interface manager selecting a final user interface template from a plurality of user interface templates stored in the one or more data storage mediums based on the final user profile; and the adaptive processor generating a user interface for display on the recipient device comprised of the final user interface template, a final set of query data from the plurality of query data and selecting the location of each element of the final set of query data within the final user interface template.

In addition, the query message may include a file with a filename, and the filename includes attributes for initial profile screening by the recipient device. The query message may also include a file with the content of the file including a plurality of attributes for profile screening by the recipient device. The profile module may create a new profile when the recipient's activities indicate one or more traits or activities inconsistent with the profile or profiles stored on the device. The user interface module may create a new user interface template when the final user profile is inconsistent with the user interface template or templates stored on the recipient device. The adaptive processor may modify the query based on the final user profile. The query data may include images, and the adaptive processor may select images for use in the final user interface based on the final user profile. The recipient profile may be a personality profile or one of the other profile types or categories identified herein The present invention also provides a method for dynamically adapting and displaying at least one query on a recipient device within a network of networked devices, the method comprising: (1) mapping, by a query processor device in communication with the recipient device, a recipient profile against a set of known profiles; and the relevancy of the at least one query to the recipient profile associated with the recipient device; (2) dynamically selecting, by the query processor, a query from the at least one query based on the recipient profile and the relevancy mapping to transmit to the recipient device; (3) generating, by the query processor, a query message including a plurality of query data including a plurality of attributes on the at least one query, a suggested query format, the suggested recipient profile, and a suggested user interface template; (4) transmitting, by the query processor device, the query message to the recipient device; (5) analyzing, by an adaptive processor on the recipient device, the query message and identifying the plurality of attributes; (6) comparing, by the adaptive processor, the plurality of attributes associated with the suggested recipient profile against a set of known profiles on the recipient device; (7) selecting, by the adaptive processor, a real-time recipient profile; (8) determining, by the adaptive processor, a final user interface template based on the suggested user interface template and the real-time recipient profile, the determining including selecting an initial user interface template from a plurality of templates on the recipient device; and (9) generating a user interface for display on the recipient device comprised of the final user interface template, a final set of query data from the plurality of query data and selecting the location of each element of the final set of query data within the final user interface template.

The method further including inserting within the query message a file and generating a filename for the file, the filename including attributes for initial profile screening by the recipient device. Further, the method could include inserting a plurality of attributes within the file associated with the recipient profile and the suggested user interface template. The method further including generating a new profile when the recipient's activities or interaction indicate one or more traits (i.e. personality) are inconsistent with the at least one profile stored on the recipient device. The method further including generating a new user interface template when the final user profile is inconsistent with the user interface template or templates stored on the recipient device. The method further including modifying the query based on the final user profile. The method further including selecting images for use in the final user interface from the set or query data, based on the final user profile. Where the recipient profile being a personality profile or one of the other profile types or categories identified herein.

The present invention also provides a device for dynamically adapting and displaying at least one query, comprising; a processor including instructions on a non-transitory computer medium, the non-transitory computer medium constituted by one or more data storage mediums. The instructions, when executed by the processor configures the recipient device to: receive at least one query message with a plurality of query data and analyzing the query message to identify a plurality of attributes; compare at least one of the attributes from the plurality of attributes from the query message with a user profile or profiles (or attributes of a profile) stored on the device; select a real-time user profile; determine a final user interface template based on the real-time user profile, the determining including analyzing a plurality of templates stored on the device using the selected real-time user profile and then selecting the final user interface template; and generate a user interface for display on the device comprised of the final user interface template, a final set of query data from the plurality of query data; and selecting the location of each element of the final set of query data within the final user interface template. The query message may include a file with a filename, the filename including attributes for initial profile screening by the recipient device. The query message may include a file with the file including a plurality of attributes for profile screening by the recipient device. The profile module may create a new profile when the recipient's activities indicate one or more traits inconsistent with the profile or profiles stored on the device. The adaptive processor may modify the query based on the selected real-time user profile. The real-time user profile may be a personality profile or one of the other profile types or categories identified herein.

BRIEF DESCRIPTION OF THE DRAWINGS

The present invention can be more fully understood by reading the following detailed description together with the accompanying drawings, in which like reference indicators are used to designate like elements, and in which.

DETAILED DESCRIPTION OF EXEMPLARY EMBODIMENTS

Hereinafter, aspects of the methods and associated systems in accordance with various embodiments of the invention will be described. As used herein, any term in the singular may be interpreted to be in the plural, and alternatively, any term in the plural may be interpreted to be in the singular. It is appreciated that features of one embodiment as described herein may be used in conjunction with other embodiments. The present invention can be more fully understood by reading the following detailed description together with the accompanying drawings, in which like reference indicators are used to designate like elements.

Figure 1:
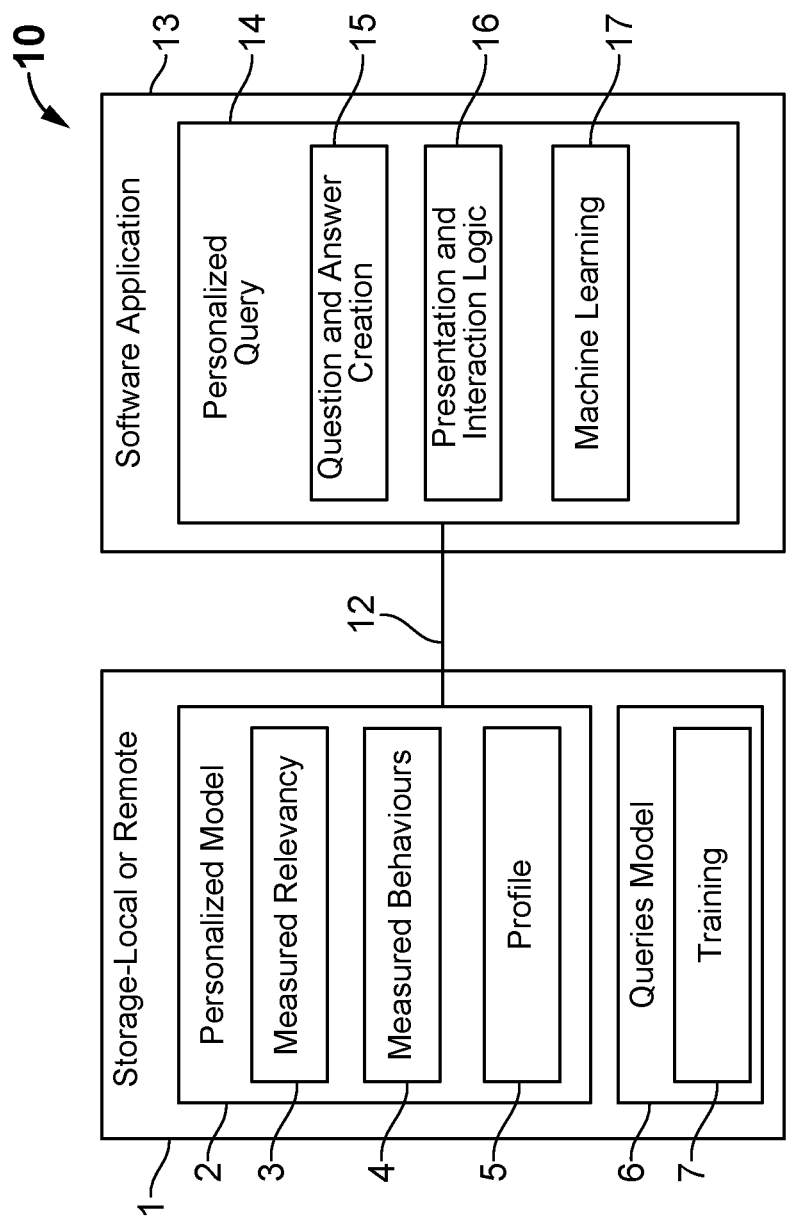
FIG. 1 depicts a high-level system diagram of an illustrative embodiment of the present invention.

As seen in FIG. 1, the present invention provides a system 10 which includes a server or cloud-based system 1 with local and remote storage capabilities. The server system 1 builds a personalized model 2 for each recipient based on the measured relevancy 3, measured behaviors 4, and the recipient's profile 5 related to a queries or content model 6. The system 10 analyzes the queries model 6 as a function of training 7 that has been provided to the system 10. The system 10 also includes one or more client devices 13 running one or more software applications. The client device 13 communicates with the server through one or more communication paths or links 12. The software application 13 works with the server-based system 1 to build and present a personalized query 14 based on the question and answer creation 15, presentation and interaction logic 16, and machine learning 17.

Through use of a myriad of known and captured data, training, varying real-world sensors, recipient interaction, and personality data and analysis, the system determines relevancy, continuously adjusts, and builds a real-time user or personality profile of the recipient or recipient of querying endpoints. The real-time personality profile is then used to select, adjust, or build the style and wording of the content or query and presentation or graphical user interface of the content or query to the recipient.

The various data elements and attributes used by the system 10 includes but is not limited to: curriculum training; personalization data; self-categorization data; traits and psychological data; physical property and ownership data; demographic data; geographic data; environmental data; physiological data; genomics data; behavioral data; activity or interactivity data; and economic data.

Curriculum training is data and content from any breadth of query, question or content, from recall and reproduction orientated queries or content which can generate quick or easy responses, to skills and concepts queries or content where the individual has detailed knowledge in a specific area like targeted health related queries, to queries or content relying on neural and cognitive reasoning networks for predictive modeling and machine learning that can be queried in a variety of ways resulting in a variety of answers or reactions. E.g. Recall related: What is your favorite color? Which could be a color palette selection. E.g. Skill related: Have you ever had a headache that was so bad that you were nauseous? Which could be a yes/no response. E.g. Neural and Cognitive reasoning related: Do you feel better in the sunlight?

Questions or content may be responded to using varying approaches, both directly and indirectly through inferring or through facial and audio recognition. Responses or reactions could also include images for answers, written response, additional sensor related data or multiple choice for instance. Responses may require the user to manually select or enter an answer. However, the response to queries are not limited to recipient interaction with the device interface. The recipient may also respond or react using voice, which the system can analyze not only for the word choice but also the frequency and tone used as a response. Further, the voice and its frequencies or signal can be analyzed to help determine the proper profile to use to ensure maximized query set participation. The recipient may further respond through an action that the device or a secondary device, such as a camera, detects. For example, the system might respond to device motion, a head nod or shake, or a thumbs up or down gesture. Responses may also be given through facial recognition to answer the query or to determine or assess the recipient's mood.

Personalization data is used to build a recipient or user profiles. The recipient profile is based upon: personality type, gender identifications, demographics, common locations, ownership, measured environment, measured physiology (i.e. vitals and genomics), measured activities (i.e. tasks), measured economy, measured behavior and relevancy.

Personality type data may include percentage complete, and other factors determine whether the system needs to further adapt the personality type using queries structured on common psychological methods for determining unique traits and considerations (e.g. OCEAN, versus Myer Briggs or other options). Personality type could be inferred through interaction. For example, the system 10 might determine the initial personality type based on whether or if the individual asks a lot of questions during consent, assuming they are going to a real individual, perhaps through email or some other means. Personality information can be inferred by how somebody wants their data to be used (i.e. just for themselves or for the betterment of society and population health). A myriad of questions and responses during setup and early interaction can be used to determine an initial or baseline personality profile. The profile can be modified, or new profiles created, based on a myriad of circumstances. Such might include time of day, day of the week, time of year, environmental or world events, or personal events and issues. Each of the questions and interaction can be used, and even required, to map to a personality through the sampling of data throughout the system.

Measured demographics data may include data regarding age, race, gender identification, affinity, ethnicity, number in household, income, military status, country of birth, citizenship, educational level, education status, marital status, pregnancy status, job position.

Measured location data may include data related to home location (primary or secondary), commitments (appointments, planning), office location (single or multiple), real-time location, location of friends and family members (living and deceased), and travel related location (vocational commuting, avocational, vacation).

Measured ownership data may include data related sources that are adjunct and available as classifiers and associated reasoning to behaviors (classes, memberships), financial influence (cars, homes), emotional and sentimental items (generational, memorable) and location identifiers (time, coordinates).

Measured environment data may include many sensing elements such as: weather sensors, sound sensors, particle sensors, gas sensors, light spectrum-heat detecting sensors, network analyzer sensors, radio communication analyzer sensors, magnetometer sensors, optical communication sensors, proximity detection sensors, position-movement sensors, and usage sensors. The weather sensors may use or sense light detection, temperature, atmospheric pressure (barometric), and capturing position of the sun and moon; sunrise and sun set; and local current weather measurement which can be augmented with regional, national, and global data. The sound sensors can be used to detect noise level, frequency identification, and transcriptive services to name a few. Particle sensors may be used to detect or measure dust particles and pollen level using particulate matter and low pulse occupancy (LPO), and smoke and mold spores by means of negative ion generator, or photoelectric light detection. Gas sensors may be used to detect gas or fumes which might have a detrimental (or positive) effect including: formaldehyde (Molecular Formula: $H_2CO$ or $CH_2O$); alcohol vapor (Molecular Formula: hydroxyl group-OH, e.g. Isopropyl-$C_3H_8O$ or $C_3H_7OH$ as well as Ethanol-$C_2H_6O$ or $C_2H_5OH$); benzene ($C_6H_6$); Hexane ($C_6H_{14}$); Liquefied Petroleum Gas (LPG) which could include a mixture of butane (Molecular Formula: $CH_3CH_2CH_2CH_3$ or $C_4H_{10}$) and isobutene (Molecular Formula: $(CH_3)_2CH\ CH_3$ or $C_4H_{10}$ or $(CH\ C_4H_{10})_2CHCH_3$); propane (Molecular Formula: $CH_3CH_2CH_3$ or $C_3H_8$); natural coal or town gas which could consist of methane or natural gas (Molecular Formula: $CH_4$); carbon dioxide (Molecular Formula: CO2); hydrogen (Molecular Formula: $H_2$); carbon monoxide or possibly smoke (Molecular Formula: CO); and oxygen (Molecular formula: $O_2$). Light spectrum-heat detecting sensors can be used to detect various environment aspects including: visual-light levels; movement; heat maps; light spectrum identification; infrared detection; UV radiation; and image recognition. Network analyzer sensors can be used to detect various network aspects including: available wireless networks; proximity; signal strength-RSSI; manufacturer information; serialization, addressing; standards-Wi-Fi, Bluetooth, Cellular; topology-MESH, Star, ring, point-to-point, bus, tree, hybrid; and network types (PAN, SAN, CAN, LAN, MAN, WAN, GAN). Radio communication analyzer sensors may be used to sense or detect: radio communication frequency; signal strength; active broadcasters; band (AM, FM, longwave, shortwave). Magnetometer sensors may be used to sense or detect: magnetic field-inductive sensing of polarity, multi-axis field strength detection, near-field communication (NFC). Optical communication sensors may be used to sense or detect: 3-dimensional positioning of sensing emitter, signal strength of emitter or emitters, and communication. Proximity detection sensors may be used to sense or detect radio signal strength feedbacks, light feedback, step responses, reactivity to nearby electro-magnetic objects and thermal heat placement to determine proximity of the recipient or devices. Position movement sensors may be used to detect or sense movement including: local position; altimeter-elevation; gravitational force; movement relative to a 3-axis accelerometer; degree of change; speed of change; and global positioning systems ("GPS" for determining global longitude, global latitude, global degree of change, global speed of change). The system may also employ usage sensors to detect usage such as electricity for individual appliances or outlets, and total electricity used, active outlets versus inactive outlets, garage door usage, open or closed doors, water leak detection, water usage, open or closed windows, car distance traveled, car operating or car off, garbage empty or garbage full, natural gas, LPG, petroleum gas, water return/waste, phone and internet usage.

Measured physiological data including vitals and genomic data may include many sensing elements such as: temperature sensors, heart rate sensors, pulse rate sensors, respiratory sensors, blood pressure sensors, metabolic sensors, circulatory sensors, neuro sensors, cardiac sensors, nerve sensors, pain response sensors, awake/sleep sensors, and health context sensors. Temperature sensors may be used to collect internal, surface level, and external temperature. Heart rate sensors may detect, or sense heart rate and heart signal characteristics based on the heartbeat and/or derived from an electrical impulse within the QRS signal. Pulse rate sensors may be used to detect, measure, or sense: the blood flowing through the circulatory system using a circulatory based sensor like Blood Pressure or a Pulse Oximeter; or collecting blood flow transit time rate in conjunction with a QRS signal or additional circulatory sensors (per location on the body). Respiratory sensors may be used to collect respiratory-breathing rate, positive airway pressure to the lungs, physiological signal of forced expiratory volume, and forced vital capacity. Blood pressure sensors may be used to measure and collect degree of stress, degree of arteries constricted (vasoconstriction), white coat syndrome, medication influenced, exercise influence, and resting state. Metabolic sensors may be used, including blood glucose sensors, to collect blood sugar levels, metabolism before/after meals, detoxification influences, and sleeping influences. Circulatory sensors may be used to detect or sense pulse oximetry as an indirect measure of oxygen saturation ($SpO_2$), a direct collection of arterial blood gases ($SaO_2$), partial pressure ($PaO_2$), tissue oxygen saturation ($StO_2$) and other $O_2$ data collection sites within the body, signal strength, and photoplethysmography (PPG). Neuro sensors may be used, including using EEG-brain sensors, to collect stress indicators, sleep indicators, and disorders. Cardiac sensors may be used, including using ECG, to collect heart activity, electrical impulses, QRS, and R-R interval. Nerve sensors may be used, including sensing the vagus nerve, and collecting resting state of the body's organs measured using vagal tone, and respiratory sinus arrhythmia (RSA). Pain response sensors may be used, including collecting salival level of cortisol, to determine pain and stress (measured for example using pain level combined with vagal tone, RSA, blood pressure and heart rate). Awake and sleep sensors may be used to collect, and measure awake and sleep data including the environmental impact (e.g. movement, audible indicators-snoring, teeth grinding, sleep talking) combined with vitals (e.g. EEG—providing cortex activity, NREM, REM, sleep depth; ECG-providing Heart rate changes; Respiration-changes, CPAP detection) and sweating (e.g. body temperature, perspiring and rate of perspiration). Health context sensors may be used to determine various health conditions including weight sensors, height through lift sensors and light detection, skin pigmentation and hair color through camera and light frequency detection, dry skin rating via electrical conductivity, dry tongue via electrical conductivity, eye dryness via camera data collection, hearing tests, and coughing via audio recording.

Measured activity data may include many sensing elements such as: food sensors, bathroom sensors, personal product sensors, shock sensors, daily task sensors, exercise sensors, travel sensors, appliance sensors, relaxation sensors, and hardware usage sensors. Food Sensors may include caloric sensors, gluten detection sensors, meal detection sensors to define, sense, or measure eating-nutrition, calories, meal status. Bathroom sensors may include using environmental usage sensor(s) of electricity, water and waste suggesting using the bathroom, toilet, or shower. Personal product sensors may sense or collect data on using a toothbrush sensor for brushing teeth, movement sensors connected to makeup or hairbrush for detecting combing hair, and feedback products like electrical stimulation for managing habitual needs (shock sensors). Daily task sensors may be used for sensing or collecting data on using a calendar, email activity, call activities suggesting working-busy day, light work day, planning to leave early/late, planning to arrive early/late, needing to focus-do not disturb; meetings-presenter, decision maker, note taker, passive listener; conversations-deeply engaged, or mildly listening; chores-mowing, auto services, home services, and personal services (purchases, healthcare checkups, dental checkups, physical and mental health-chiropractic, massages, acupuncture, therapist, community groups). Exercise sensors may be used to sense or collect data including equipment reporting-workout time, intensity, calories burned, energy level, and category including weights, cardio, and yoga. Travel sensors may sense or collect data from emails, travel applications, environment sensors detecting indirect traveling (i.e. someone else is doing the work), and direct traveling (i.e. driving, cycling, rowing, running). Appliance sensors may be used to detect or sense using fridges and ovens to describe level of cooking-status as engaged, lightly engaged, not engaged; or using the clothes washer, clothes dryer, dishwasher for chores detection along with increased water usage and electricity changes. Relaxation, meditation and sleep sensors may be used including EEG-based sensors, audio detection, motion detection, to determine various duration, status, depth, and suggestions. Hardware usage sensors may be used to passively collect data on usage of devices from sensors from mobile phones, portable audio devices, hands-free voice recognized playback and internet driven cognitive computing devices, televisions, tablets, e-readers, hubs and providing a collection of information on charging, battery level, screen usage, interactions-touch, buttons, frequency, patterns, number of apps, app classification, app usage, call log, email usage, SMS usage; and self-reported hobbies.

Measured economic data may include many sensing elements such as: news related sensors, work-life balance sensors, finance related sensors, and hospital or care related sensors. News related sensors may include web crawling and news media feeds for cognitive computing of news with reporting based on current location, surroundings or home, and friends' locations to define recipient recognizable personalized global tragic events, global heightened security, global impact level and national tragic events, national heightened security, and national impact level; local tragic events, local heightened security, and local impact level. Work-life balance sensors or data may be collected through calendar, globally available calendars, and suggested activities planned in relation to work-life balance, by measuring holiday-working and related stress; weekend-working and related stress; travel impact-cancellations, planned departure, delays, arrival times traffic-heavy traffic on route, crashes, police; and closures of an office or school. Finance related sensors or data may be collected through personal finance companies that the recipient provides access for assessing financial-gains, losses, stocks, investments, upcoming bills to pay, risks in due dates and running tight of funds for the month. The measured economic impact may also include hospital or care related sensors and data collected through media, calendars, emails from hospitals or care providers including data on hospitalization, births, deaths-importance, and impact level.

Measured behavioral data may include recipient and query-dependent actions, voice, facial and body recognition, including: user-computer reported actions for skipped queries—quantitative and qualitative reasoning on preferential alignment and emotive self-identification and reasoning; interactivity with the queries—patterns, heatmaps, usage transactions, evaluation time and avoidances; abandoned queries—whether timed out, ignored, or disabled; completed queries—quality of response (authenticity, valued—more like this, less like this), response patterns (e.g. same answer for similar questions), durations (answer latency); insights and lookups—transactional cues to educating response based on reported information, such as live tiles, links and references, and alignment predictors; and rating—crowdsourced, classifications (based on personality, or relevance) and prior personalized trending responses; activities with other systems, sensors, applications and functions of the query reporting equipment; tonality of the voice during audible response—emotional states and attitudes (normal, sad, calm, bored, angry, panicked, joy, fear, stress, stability, neuroticism), personality (introverted, extroverted), deception, gender classification, age, physical size, prosodic characteristics (timbre, salience, pitch, rate, loudness, intensity, crackling); facial and body recognition—such as micro-expressions (surprise, fear, disgust, anger, happiness, sadness, contempt, hate) using interrogation techniques such as the Reid method, and paralinguistics (facial expressions, gestures, body language, eye tracking).

Measured Relevancy Data may include both perceived and likelihood to respond meaningfully to queries and includes: classification and estimated likelihood; and contextual and estimated likelihood.

The present invention uses the data or data sets, as described herein, to create categorical based recipient profiles or to enhance one or more recipient profiles. The system uses the data to identify attributes and characteristics of the data and how the data impacts the recipient's behavior (i.e. if and how they respond to queries). The data and the mapping of the data to the recipient and query relevancy are primarily categorical. The categories, as mentioned above, include, but are not limited to: curriculum training; personalization data; personality type data; self-categorization data; psychological data; measured demographics; location data; ownership; environmental; physiological/genomic data; activity data; economic data; behavioral data; and relevancy data.

Figure 2:
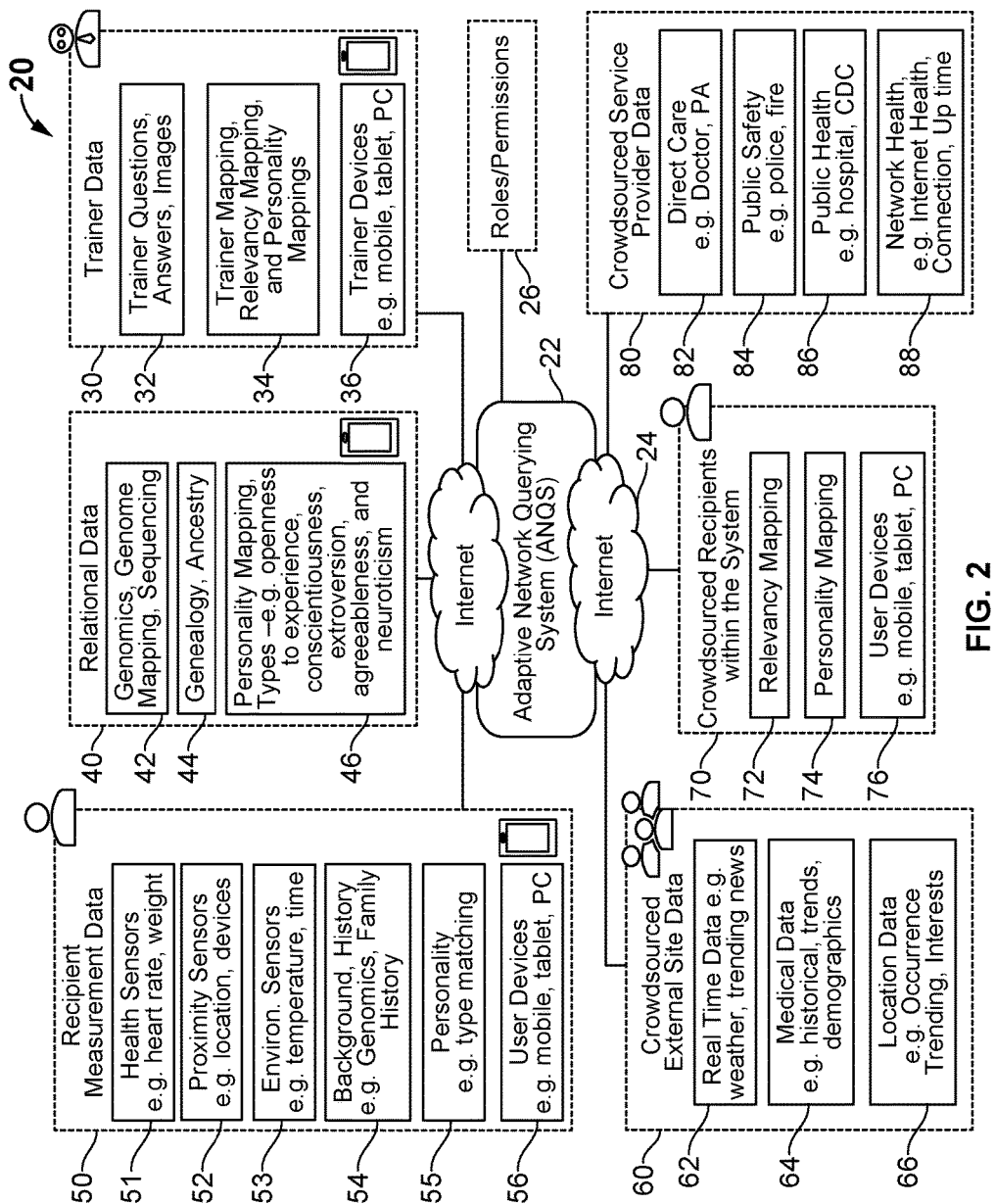
FIG. 2 depicts a more detailed system diagram of an illustrative embodiment of the present invention.

As shown in FIG. 2, the System 20 utilizes significant amounts of data to adapt the query system. The Network 20 of the present invention includes the Adaptive Network Querying System 22 which is connected via internet 24 or other communication methods to numerous devices and data. These devices and data segments include trainer devices and data 30, relational devices and data 40, recipient measurement devices data 50, external crowdsourced data 60, internal or system crowdsourced recipient data 70, and crowdsourced service provider devices and data 80. The Adaptive Network Querying System 22 is also accessible by one or more admins and users having roles and permissions as set forth in the systems roles and permissions sub-system 26.

Within the trainer data 30, therein includes trainer questions, answers and images 32, a trainer mapping, relevancy mapping and personality mappings element 34, and trainer devices 36, such as mobile devices, and tablets.

The relational data 40 includes genomics, genome mapping and gene sequencing data 42, genealogy (genes, carrier, traits, risks) and ancestry data 44, and personality mapping data 46. Personality mapping data 46 may include data on personality types, such as whether a recipient is open to experiences, consciousness, extroversion, agreeableness, neuroticism, and other known types.

The recipient measurement section 50 includes health sensors 51, proximity sensors 52, environmental sensors 53, background data 54, personality data (type matching) 55, and recipient devices 56. Health sensors 51 might include things like heart rate and weight monitoring of data and would provide physiological data measurements. The proximity sensors 52 might include things like location sensors and devices with location tracking data and would provide activity related data measurements. The environmental sensor 53 would include sensors measuring temperature, time, passively sensed, ancillary, or other directly report data sources relevant to contextual cues and measured environment data. The background and recipient historical data 54 might include specific longitudinal history of the recipient, including genomics, and family history. The personality data 55 might include personality type matching information. Recipient devices 56 might include the types of devices such as mobile, tablet, pc, the operating systems within those devices, and how they are used and the device as a sensor.

The external crowdsourced section 60 might include real time data 62, medical data 64 and location data 66. The real time data 62 might include data such as weather or trending news, and would provide economic related data measurements. The medical data 64 might include historical data, trending data in terms of population (upward and downward risks, emerging, outbreaks, epidemic, and pandemic) and demographic data. The location data 66 might include occurrence data, trending data, and interests.

In addition, the system may include internal or system crowdsourced data 70 of recipients include relevancy mapping 72, personality mapping 74, and recipient devices 76.

Further, the crowdsourced service provider data 80 may include direct care 82, public safety 84, public health 86, and network health 88. The direct care 82 would include devices and data for direct care provides such as information that is de-identified by a recipient's doctor or physician's assistant. Public safety 84 would include devices and data such as police and fire or water and power through varying channels like public broadcast information. Public health 86 would include devices and data such as local hospitals, ambulatory and CDC information. The network health 88 would include devices and data based on internet connections, internet or provider health, uptime, and other similar network and communication-based information.

The network 20 includes interaction amongst trainer section 30, relational section 40, recipient measurement section 50, external crowdsourced section 60, internal crowdsourced recipient section 70, and crowdsourced service provider section 80 as used by the Adaptive Network Querying System 22 to help formulate ideal queries or content based on relevancy mapping 72, personality mapping 74 and other recipient-based elements to provide system determined queries or content relevant and related to the recipient.

Figure 3:
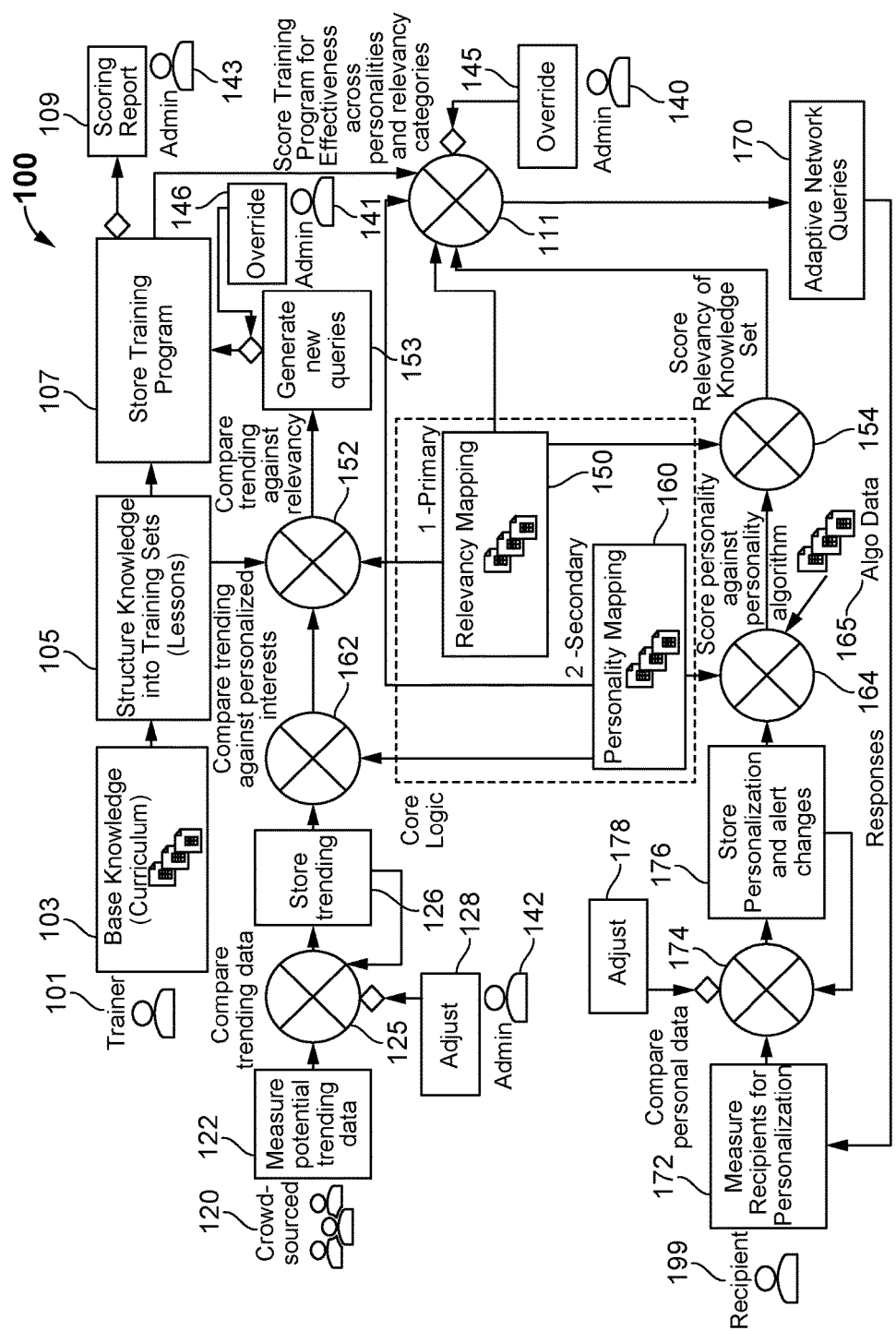
FIG. 3 depicts a flow diagram utilized by an illustrative embodiment employed by the present invention.

FIG. 3 provides a high-level network flow of data through the system 100. It integrates permission roles of admins 140, 141, 142, 143, with one or more trainer roles 101, crowdsourced role information 120, and the recipient role 199. The admins 140, 141, 142, 143 have the ability to override any existing function of the system such as ignoring relevancy for delivery or stopping new queries from being automatically accepted into the machine learning environment. The admin review reporting mechanism looks at data modeling for saturation and performance while distributing new tasks to trainers 101. Trainer 101 could also be an admin. Trainer 101 injects and maps new content with new classifications to drive a higher scoring for relevancy across varying dimensions of recipients 199. These new classifications are mapped in a way that can be re-used when automatically collecting new trending data points from crowd-sourced 120 information sources. The crowd-sourced data 120 derives new questions and content to improve relevancy through machine learning and adapting to a changing landscape of health and world conditions. These new questions can be actively injected into the overall training program for new queries or they can be sandboxed with acceptable rules set by Admins 140, 141, 142, 143 to ensure a high degree of relevancy to the pool of questions intended for the recipients 199. The recipient 199 can provide both a passively sensed signal that helps correct the alignment and relevancy, while also providing an active feedback loop on queries based on behaviors and personality.

Proceeding through the flow, the trainer 101 establishes base knowledge curriculum 103 which is used to structure knowledge into training sets or lessons 105. These training programs are stored in step 107 and can ultimately provide feedback for a scoring report 109 to an admin 143. The crowd-sourced data 120 can be utilized and in step 122 can measure potential trending data. The trending data 122 is compared in step 125 and can be adjusted in step 128 by an admin 142. Through the comparison of trending data 125, the system then stores trending data 126 and the data can be compared against personalized interests in step 162. The structured knowledge training sets or lessons 105 can also be compared against trending relevancy in step 152.

The relevancy mapping 150 is also used in the comparison against trending relevancy in step 152. All recipient's personality mapping 160, which includes individual recipients 199, can be used in the comparison step 162. Based on the comparison of crowd trending data against all recipient's personality mapping 160 in step 162 and the comparison of trending data against all relevancy mapping 150, which includes individual recipients 199, in step 152, the system can generate new queries in step 153. Admin 141 would have the ability in step 146 to override any new queries.

In addition, the system 100 can measure the recipients 199 for personalization in step 172. The personalization is utilized in a comparison step 174 against stored personalization information 176. An admin 142 can also adjust, in step 178, the personalization comparison parameters used in the comparison 174. The personalization is stored in step 176 and can be used in conjunction with the comparison step 164 which uses an individual recipients' personality map pulled from all recipient's personality mapping 160 against recipient-based personalization from steps 172, 174 and 176. The comparison in 164 scores personality against the personality algorithm including the algorithm data 165. The individual recipient's relevancy map pulled from all recipient's relevancy mapping 150 is then also compared, in step 154, against the score personality from step 164 in determining a score relevancy of the knowledge set. The score personality from 164 and the score relevancy from step 154 are then used to score training programs in step 111 for effectiveness across personality and relevancy categories. This score training comparison in step 111 also utilizes the relevancy mapping 150. The score training comparison in step 111 can also have various overrides from step 145 which might be implemented by an admin 140.

Ultimately, the personality mapping 160, the relevancy mapping 150, and the score training program 107 compared in step 111 are fed to the Adaptive Network Queries 170 which displays queries to the recipient and receives responses. Such responses can be fed back into step 172 for measuring the recipients for personalization. Through use of the system 100, the training programs 107 and mappings 150, 160 can generate query programs which are effective for the specific recipient 199 based on the recipient's personality and relevancy to the questions.

The information flow may best be described using a set of queries going from end to end through the system. By way of example, a query set may be defined as a question, a set of responses and insights that are presented after the recipient responds to the question. The insights consist of text, graphics, live feeds and data visualization content components. A system administrator, or a trainer, establishes ground truth by programmatically loading the individual components of the query set including the recipient or user interface templates into the system via a content publishing system such as a web-based, command line or dedicated client application. The templates include parameters such as the question type (multiple choice, etc.), maximum number of response options, max text length per question and response, max image size, data visualization type displayed after the response is indicated, comparative definitions of the recipient response with responses from the population or sub-population for added insight to the recipient, and max text length for a text-based insight displayed after the response is indicated. The properties of the templates also determine the recipient or user interface details that govern the format of the queries, and specific content such as—font details, padding, positioning, text and the image, etc.

Through the system, the admin/trainer uploads many (hundreds or thousands) of question sets, via pre-formatted files (such as delimited formats like CSV) in a batch upload or other applications. The uploaded file can help identify the template number to assist the system in matching each question set to a preferred template.

The admin/trainer is able to execute each query set on the admin interface and is able to modify the content (text and images) to drive scoring categories from the ground truth. The admin then publishes the query set or group of query sets. The query sets can initiate a data transfer of the new query set to the end recipient's client. The system utilizes algorithms to calculate relevancy and personality scores for the different query sets. The relevancy scores are calculated on the server and are periodically delivered to the client where they can be stored locally along with the query set parameters and content. The client and server interfaces collaborate and use the relevancy scores and personality scores to determine the sequence of the query sets to the recipient and whether to hide any particular query set. When the end recipient interacts with the query set, via the recipient interface or user interface, the system records the recipient's behaviors among other measured data and associated metadata and sends the recorded data back to the server. Although measured data can be sent at any time, it is important to collect the contextual data at the time of the query response. The admin user can view the calculated weightings for a particular query set and can override the calculated score in order to manually drive sequence priority or show/hide specific queries.

Figure 4:
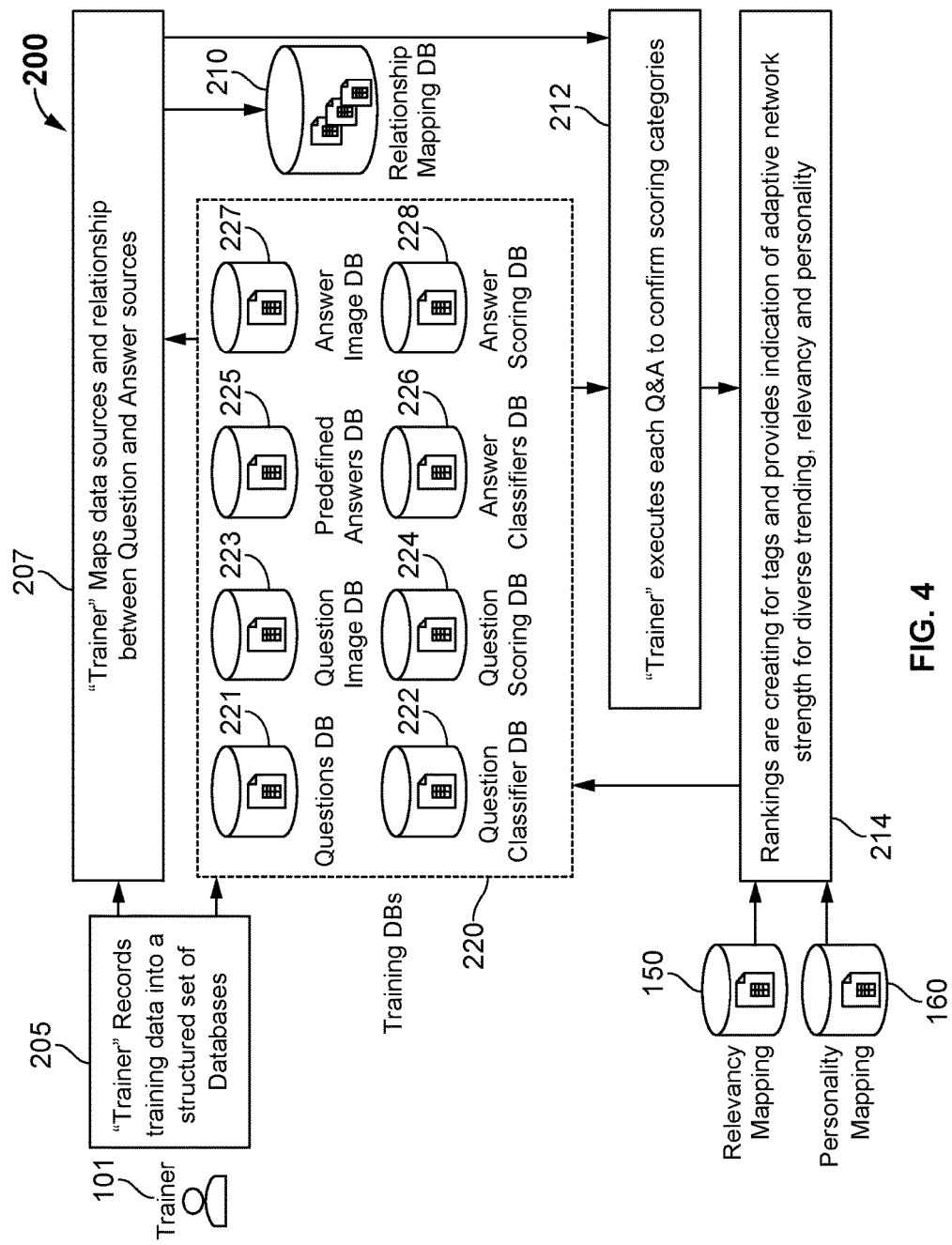
FIG. 4 depicts a flow diagram of the query trainer aspects of an illustrative embodiment employed by the present invention.

FIG. 4 provides that the process flow 200 detailing the trainer-based data installation through analysis and integration of relevancy mapping 150 and personality mapping 160. The trainer 101 records training data into a set of structured databases 205. The trainer then establishes ground truth by mapping these data sources and the relationships between query sets for questions and answer sources in step 207. The relationships are then mapped and stored in a database 210. In addition, the trainer sets up various training databases 220 and those databases may include a questions database 221, question classifier database 222, question image database 223, question scoring database 224, pre-defined answer database 225, an answer classifier database 226, an answer image database 227, and an answer scoring database 228. These training databases 220 are in communication with the mapping data sources and relationship data 207 and are also tied to the trainer executing each question and answer to confirm scoring categories in step 212. Based on these scoring categories 212, rankings are created in step 214, including creating tags which provide an indication of the adaptive network strength for a diverse set of trending, relevancy and personality. These rankings integrate the relevancy mapping 150 of the queries as well as the personality mapping 160 of the recipient. The queries need not be questions and could be content in non-query format.

Once the information is mapped and ground truth established, it is executed to ensure that there is sufficient coverage for the confidence levels across varying relevancy mapping 150 and personality mapping 160. These confidence levels translate to scored rankings which in turn can be used to further develop the system through crowd-sourced trending. If a certain demographic, age, location, gender identification, or other attribute is under-covered, meaning coverage does not meet an expected quantitative limit, then it can be prioritized for additional automated training through external linkages. Further, the system can calculate a relevance score for each question set that is associated with a particular recipient and a relevance score that is independent of the recipient. The Recipient Specific Relevance Score ("RSRS") considers the specific recipient's context, such as inferred levels of engagement, the history of the particular user's interactions with the query sets. The RSRS may also classify recipients into groups of similar or related recipients. The Recipient Independent Relevance Score ("RIRS") accounts for what topics are trending nationwide and calculates a score based on how closely the topic of the question set matches the trending topic. The RIRS further accounts for the inferred level of engagement from the population of recipients as a whole (i.e. whether people in general are interacting with the questions set). If the topic is trending and the recipients are interacting with the question set, then the RIRS will be high and if the topic is trending but recipients are not interacting with the question set then the RIRS will be lower. The RIRS and RSRS are used to calculate the total relevance score ("TRS") which directly drives the end recipient experience with a particular query set.

The relevance scores are computed by analyzing the recipient's behavior and other measured data, recipient responses, question properties, trending and other crowd-sourced data, and past relevance. The recipient behavior analysis includes behavior measured data such as how the recipient interacted with the question, was it abandoned or completed, or did the user click on the insight link for more information. The recipient response data is used to analyze the existing recipient profile data, and other longitudinal and collected measured data of a particular recipient. The question properties may refer to a specific template or UI form, question type, contextual tags, length of questions, number or response options, and the insight visualization type. Trending linkages involves an analysis of the linkage between the question topic area and the topics that are currently trending, and the trending is assessed on a global, national regional and local scale.

Using the relevance score, the system or network makes automatic adaptions for the recipient. These adaptions can change the experience for specific recipient s or groups of recipient s or all end recipient s, change the sequence/priority of questions, remove a question or set of questions from circulation, hide a question or set of questions from a subset of recipient s, change the visualization type in the insight for a question template, and change the reading level. The relevance score will be stored in the analytic database that includes the inputs, outputs, automated system actions, manual actions and algorithm versions. The database will further store calculated relevance scores of each question, calculated relevance scores of strengths of trending linkages, and offer exportable reports.

The goal of the systematic questions is to allow the network to infer relations between varying topics and to suggest further queries based on responses from one question to the next. Queries can cover many topics. For example, they may cover aspects related to wellness, health and quality of life. These health queries may go to the fundamental foundation of overall wellness of the recipient narrowing the focus on the health of recipients' mind and body to assess wellness. Overall health of the mind and body are determined with queries dealing with basic survival needs, mental health and sleep revitalization. Mental Health, sleep revitalization and basic survival needs are assessed with queries based on the recipient's cognition, exercise, diet and nutrition. The overall health of these topics are assessed using queries which assess the recipient's neuro state, cardio respiratory and metabolism. These categories can be assessed based off queries related to chronic diseases and risky behavior such as working too much, sleeping too much, eating too much, etc. Which can be assessed based on questions of about recipient's health care, which can be assessed using general quality of life queries.

Figure 5:
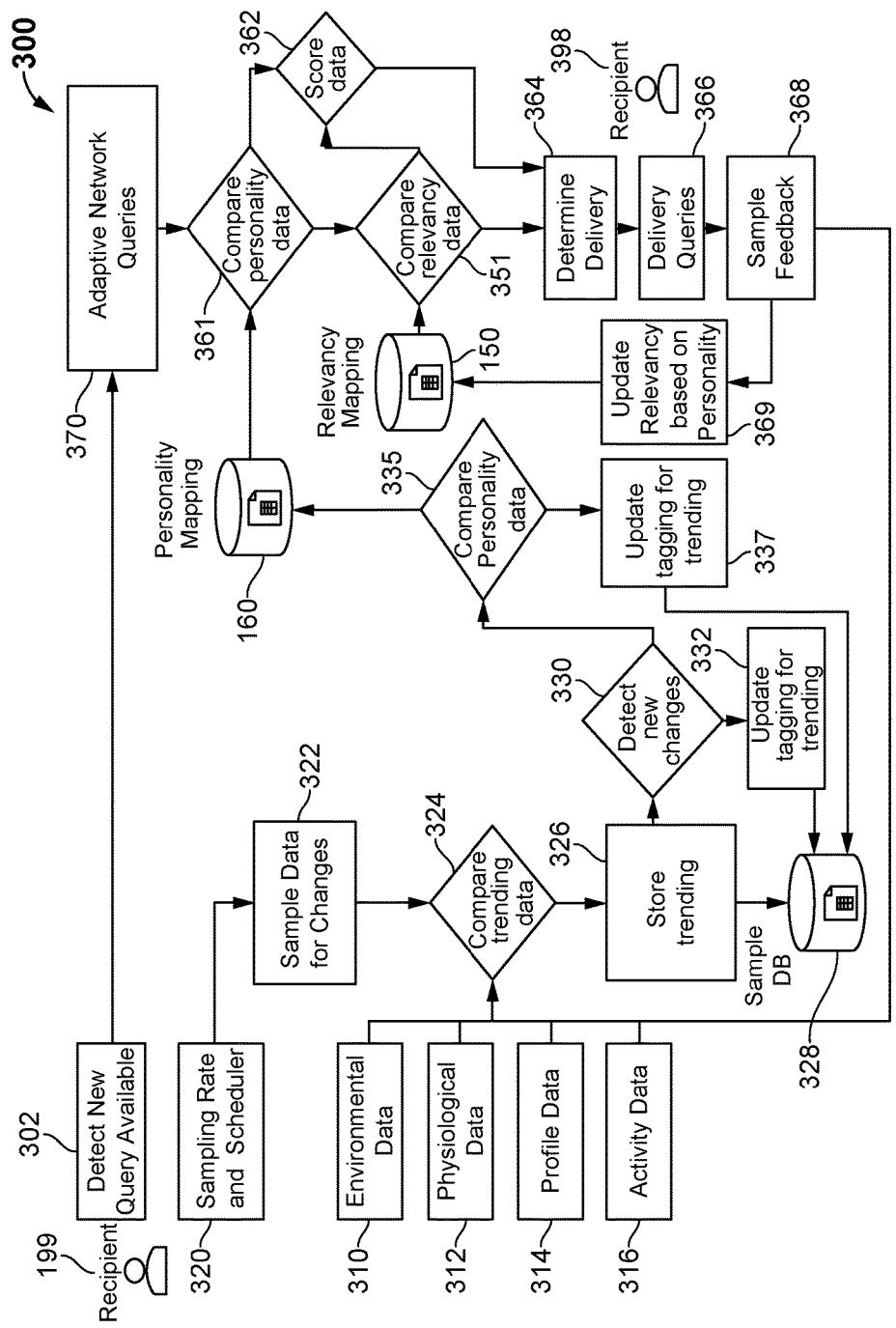
FIG. 5 depicts an additional flow diagram including relative inputs of an illustrative embodiment of the present invention.

FIG. 5 presents an additional flow 300 with the recipient 199, through the client device, detects a new query 302 and depending on the availability of the query a scoring is triggered on the information available and ultimately delivered. The Adaptive Query Network 370 then compares personality data in step 361 using the personality mapping 160 of the recipient 199. In addition, relevancy mapping 150 is also utilized in a relevancy data comparison in step 351. Ultimately, the personality data comparison 361 and the relevancy data comparison 351 are used to score the data in step 362. The personality data comparison 361 and the relevancy data comparison 351 and the score data 362 are all utilized to determine the delivery in step 364, the actual delivery of queries in step 366 to the recipient 398. Feedback is provided in step 368 which is then used to update the relevancy based on personality in step 369. This updated relevancy is then used to update and/or enhance the relevancy mapping 150. In addition, the feedback along with additional data including environmental data 310, physiological data 312, profile data 314, and activity data 316 are used to compare trending data in step 324. The trending data comparison 324 may interact with a sampling rate and scheduler 320 which determines how often sample data from the external sources change in step 322. The comparison of tending data in step 324 is then stored in step 326 which is stored in one or more sample databases 328. The system 300 also looks within the trending data to detect new changes in step 330. The data with changes is then updated and tagged in step 332 to identify more relevant trending data. In addition, the new changes identified in step 330 are then also used and compared against the personality data in step 335. The personality data comparison 335 can be used to update or supplement the personality mapping 160 as well as update specific tagging and trending data specific to the personality data in step 337. The updates can be stored in one or more databases 328. Through this scenario, a recipient 199 can have relevant queries based on their personality mapping 160 and relevancy mapping 150 taking into account the various data, 310, 312, 314, 316 which factors trending data as well as the recipients specific profile in relation to both the queries and trending data at the current time of the query.

Figure 6:
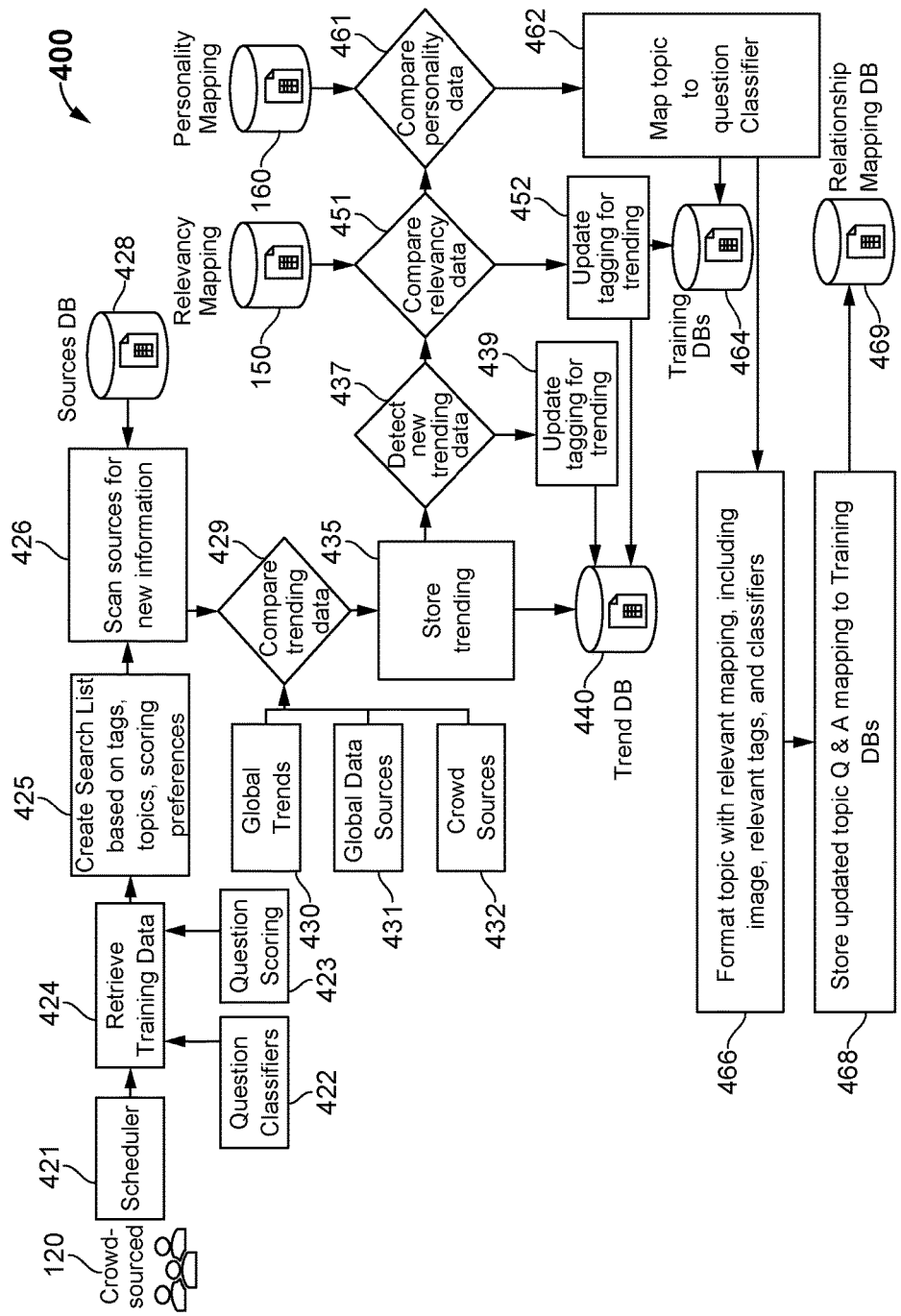
FIG. 6 depicts an illustrative flow diagram for query refinement based on relevancy and personality mapping of the present invention.

As seen in FIG. 6, the present invention also integrates the use of crowd-sourced data 120 which can be received into the system 400 through one or more external sources. The crowd-sourced data 120 and information can utilize existing training to generate new queries and responses. The crowd-sourced data 120 interacts with a scheduler 421 in which the system 400 can retrieve training data 424 which includes question classifiers 422 and question scoring data 423. The system 400 then creates, step 425, search lists based on tags, topics and scoring preferences in step 425. In step 426, sources are scanned for new information. Such new information would include data from source databases 428. The system then compares the trending data in step 429 with global trend data 430, global data sources 431, and crowd-sourced data 432 which are compared in step 429. The comparison 429 then stores the trending data 435 including storing it in the trend database 440. The crowd-sourced data compared against global trending data is then analyzed to detect new trending data in step 437. The system 400 can then update and tag this trending data in step 439 and save it in an appropriate database 440. Ultimately, the detection of new trending data 437 is then compared against relevancy data 451 and personality data 461. The relevancy data comparison 451 utilizes the relevancy mapping 150 while the personality data comparison 461 uses the personality mapping 160. Through the relevancy data comparison 451 and personality data comparison 461 the system then can map topics to questions and classifications or classifiers in step 462 leading to the system identifying an appropriate format topic based upon relevant mapping including suggestions on relevant images, relevant tags, and relevant classifiers in step 466. The system 400 then stores the updated topic, question and answer mapping to the training database in step 468 which is then also used to update the relationship mapping database 210. It is important to note that the relevancy data comparison 451 and personality data comparison 461 also lead to updating the trending database and the training database 464.

The present invention also uses machine learning in addition to crowd sourced data to generate new queries and responses. The Adaptive Network Query System has a machine learning component that uses artificial, computer generated, users to categorize and assess new queries. After the system processes the new queries through the artificial recipients and how the artificial recipients have responded to the queries, the system will categorize, tag, and map (relevancy and personality) the responses. As the new queries are released, the artificially catalogued responses will be further refined as the recipients interact with the queries. Further, as actual recipients expand. the total profiles available will also expand the artificial profiles used by the machine learning function.

However, the system structure need not be traditional server-side architecture. The system could employ systemless or unbounded design. This unbounded design means the system could employ virtualization, containerization, or other solutions to create independence from specific architecture, software, cloud, or other features.

Figure 7:
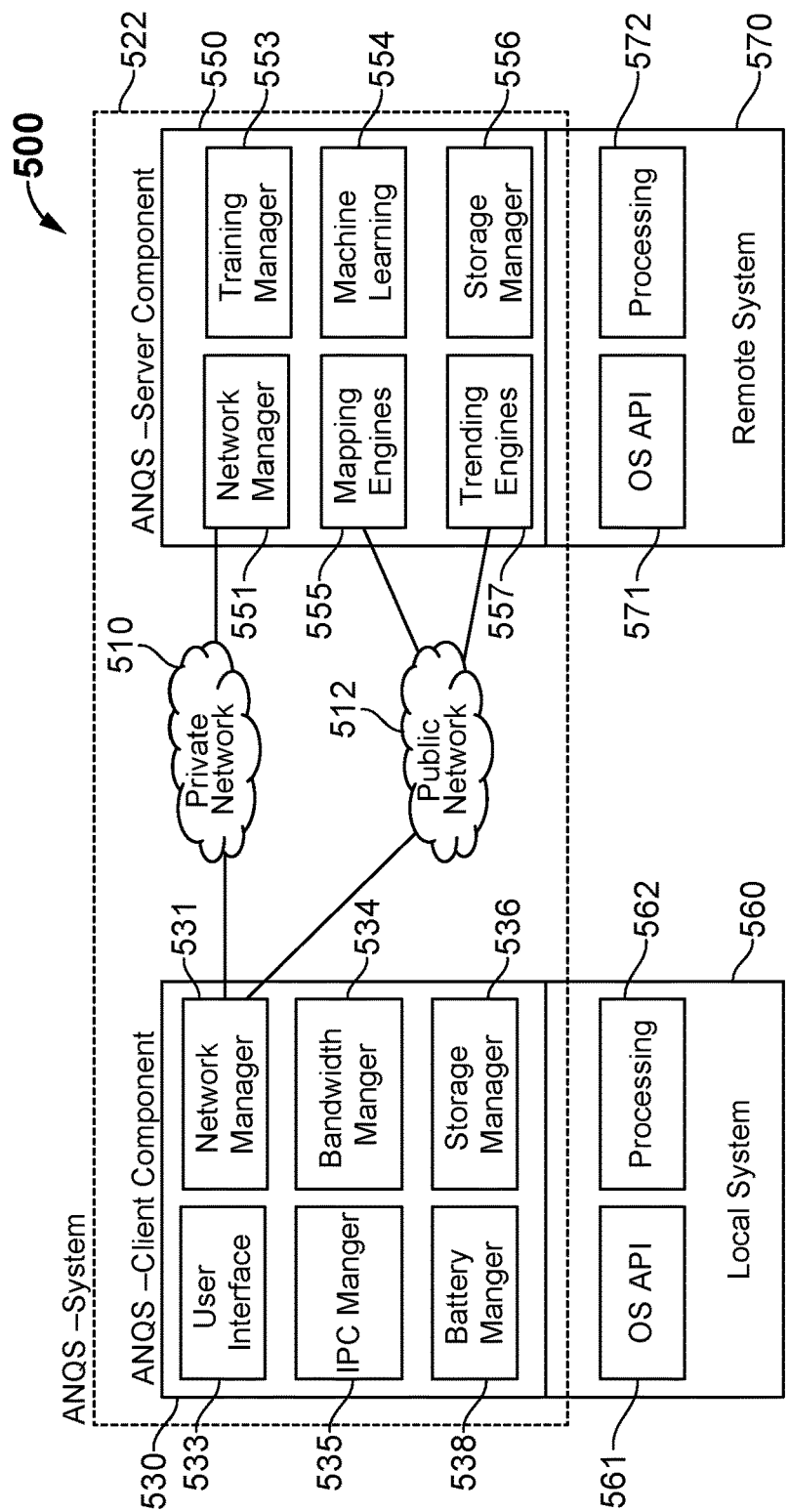
FIG. 7 depicts a system diagram of the multi-manager system of an illustrative embodiment of the present invention.

As seen in FIG. 7, the Adaptive Network Query System ("ANQS") 500 includes the ANQS client component 530 and the ANQS server 550 which form part of the network 522. The client 530 may be connected to the server 550 via a private network 510 or a public network 512. The client 530 includes the network manager 531, the recipient or user interface 533, the bandwidth manager 534, the inter-process communication (IPC) manager 535, the storage manager 536, and the battery manager 538. The server side 550 includes a network manager 551, a training manager 553, the machine learning component 554, the mapping engines 555, the storage manager 556, and the trending engines component 557.

The client 530 also includes the local system or platform 560 which includes one or more processing components 562 and transactional communication component 561 such as an Operating Systems (OS) API functionality as a given example method for transactional communication between the ANQS Client Component 530 and the local system 560. The local platform 560 of the client 550 includes all appropriate processing elements to process and manage the client components 531, 533, 534, 535, 536, 538. The server side 550 includes the remote system or platform 570 which includes one or more processing components 572 and a transactional communication component 571 such as an Operating Systems (OS) API functionality as a given example method for transactional communication between the ANQS Server Component 550 and the remote system or systems 570. The remote system 570 also has additional elements to process the server-side components 551, 553, 554, 555, 556, 557.

The client component 530 receives updates from server component 550. The client network manager 531 has configuration controls that the local inter-process ("IPC") manager 535 can utilize to improve bandwidth usage, battery usage and storage usage through their respective managers 534, 536, 538. The IPC manager 535 coordinates activities, bandwidth, storage, and battery on a local system 530 in conjunction with the remote server system 550. The IPC manager 535 reduces the information between the server 550 and client 535 and the customization to the individual personalization and relevancy.

A set of configuration controls that are retrieved from the server 550 and are managed within the client 530 within its profile manager defines a client profile which includes many areas of managed user data for classifying appearance, perception of relevancy, and personality. Included in this profile, is a client hardware represented model which the IPC utilizes to improve usefulness of the hardware to the recipient without overloading and stressing limitations for reduced performance and brand satisfaction. Some example client hardware profiles include: optimized for low power, optimized for metered connections, optimized for small storages, balanced optimizations options, and high performance. A high-performance profile may store less and require more power and bandwidth than other profiles, with the gain that the content delivered is fast and fresh. Whereas, a balanced option may be customized to the hardware and can vary from mobile hardware models to performance IoT gateways to low power wearable gateways. In contrast, a system that is always plugged in may not include a profile for battery. A system that is a flagship mobile with very large storage capacity may not have storage concerns. A system that is a wearable gateway may have a high degree of concern on battery usage. Further, characterization of network and storage access may suggest in some cases that large content processing from a local storage may be more battery intensive that network processing and may allow for limited storage while focusing on network protocol proficiency such as tradeoffs in Wi-Fi versus Cellular, versus Bluetooth Low Energy. Further, any consideration on the configuration controls changing may be based on the recipient and their Personality Mapping/Relevancy Mapping (not the type of device); time of day; historical recipient interaction (low power in evenings; high performance in mornings) and other factors and attributes.

As previously discussed, the Personality Mapping and Relevancy Mapping will impact both the Profile Manager and the Recipient or User Interface Manager. The inferred result of the personality mapping may hide, arrange, or replace UI components. These UI components may be stored locally but would require profile changes to adapt to new network requirements if the UI builder requires a new set of information, or live feeds based on the ability to complement their needs.

Live feeds are a mechanism for providing dynamic content to help recipient engagement and responsiveness to varying lines of queries. In some cases, live feeds can provide an educational tool to the query for the recipient to increase their skillset in response and responsiveness. Live feeds can also be relevant to the user to describe current local events such as news feeds, weather, public health information and safety information. In addition, as part of insights, live feeds can provide useful go to information that the recipient can utilize for scoring and future queries.

Further, FIG. 7 shows the information flow of server 550 and client 530 communication related to the ANQS system 500 with the client 530 receiving communication by the server-side network manager 551 to the client-side network manager 531. The client 530 receives a configuration based on its overall hardware, a dedicated IoT gateway versus a mobile phone will have customized configurations that would be received during an initial communication with the server. These profiles can be locally customized on the hardware through adaptive needs of the system or recipient preferences, needs and other situations like system overrides from an administrator.

These configurations define controls that the IPC Manager 535 uses to balance the usage of content storage, and requests to the network manager 531 for more information on an as needed basis versus always needed basis. The IPC Manager 535 receives updates from the bandwidth manager 534 to produce a larger number of updates if the system 500 is using a high bandwidth non-metered connection. The IPC Manager 535 and Bandwidth Manager 534 and also reduce the update requests if the connection becomes metered or the bandwidth reduces which can cause downstream lag to the recipient from a recipient or user interface perspective. A larger number of API requests and content requests over a slower connection will also consume more power due to processing needs and likewise battery usage. Thus, the battery manager 538 is used to report the battery usage as an additional measure to the IPC Manager 535 to help with balancing the needs of the system 500 with the configuration of ANQS client 530.

Figure 8:
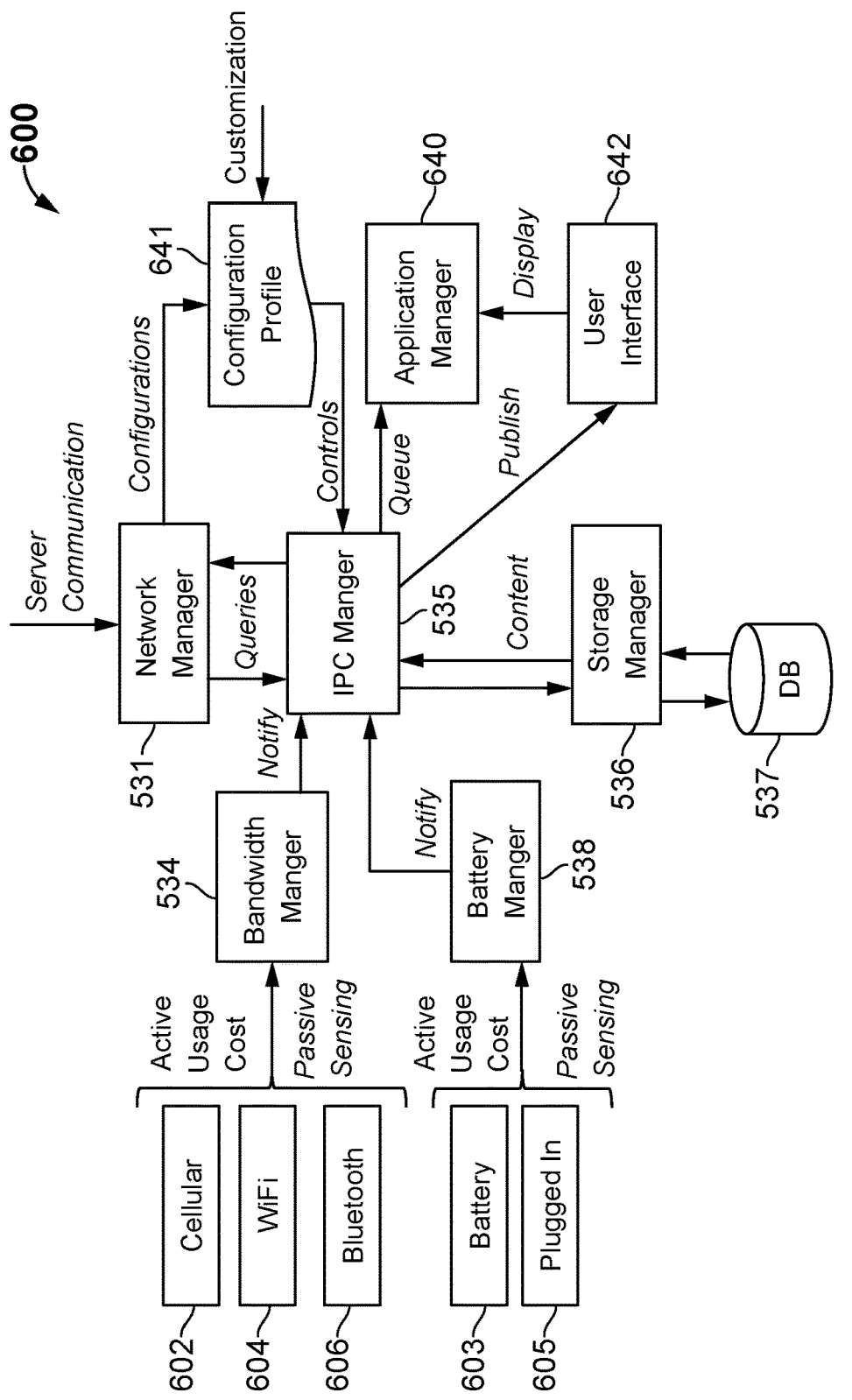
FIG. 8 depicts a system diagram of the client-side system of an illustrative embodiment of the present invention.

As seen in FIG. 8, the client side of the present invention includes additional elements from those shown in FIG. 7. The client 600 includes the network manager 531, the IPC manager 535, the storage manager 536, the battery manager 538, and the bandwidth manager 534. In addition, the client 600 includes the network manager 531 interacting with one or more configuration profiles 641. These configuration profiles 641 help determine configurations of both the client device as well as configuration of the recipient. The configuration profile 641 is used by the IPC manager 535 to identify and set up various controls related to the device 530 and is used by the network manager 531. In addition, the IPC manager 535 interacts with an application manager 640 to identify and publish the appropriate recipient or user interface 642.

The bandwidth manager interacts with and passively senses data about the cellular network 602, the WIFI network 604, and Bluetooth communication 606. The battery manager 538 interacts with the battery 603 and any passive sensing of the status of whether the client 530 is using the battery 603 or is plugged in 605. Ultimately, the client 530 through the IPC manager 535 can identify and determine, based on the configuration profile 641 and the application manger 640, an optimal recipient or user interface 642 taking into account the bandwidth manager 534 determination of bandwidth availability and the battery manager 538 sensing and determining the optimal power consumption.

Though use of the configuration profile 641, the IPC manager 535 can determine if queries presented to the recipient or user interface 642 presented to the recipient need to be modified based on the bandwidth, battery, and configuration profile.

Figure 9:
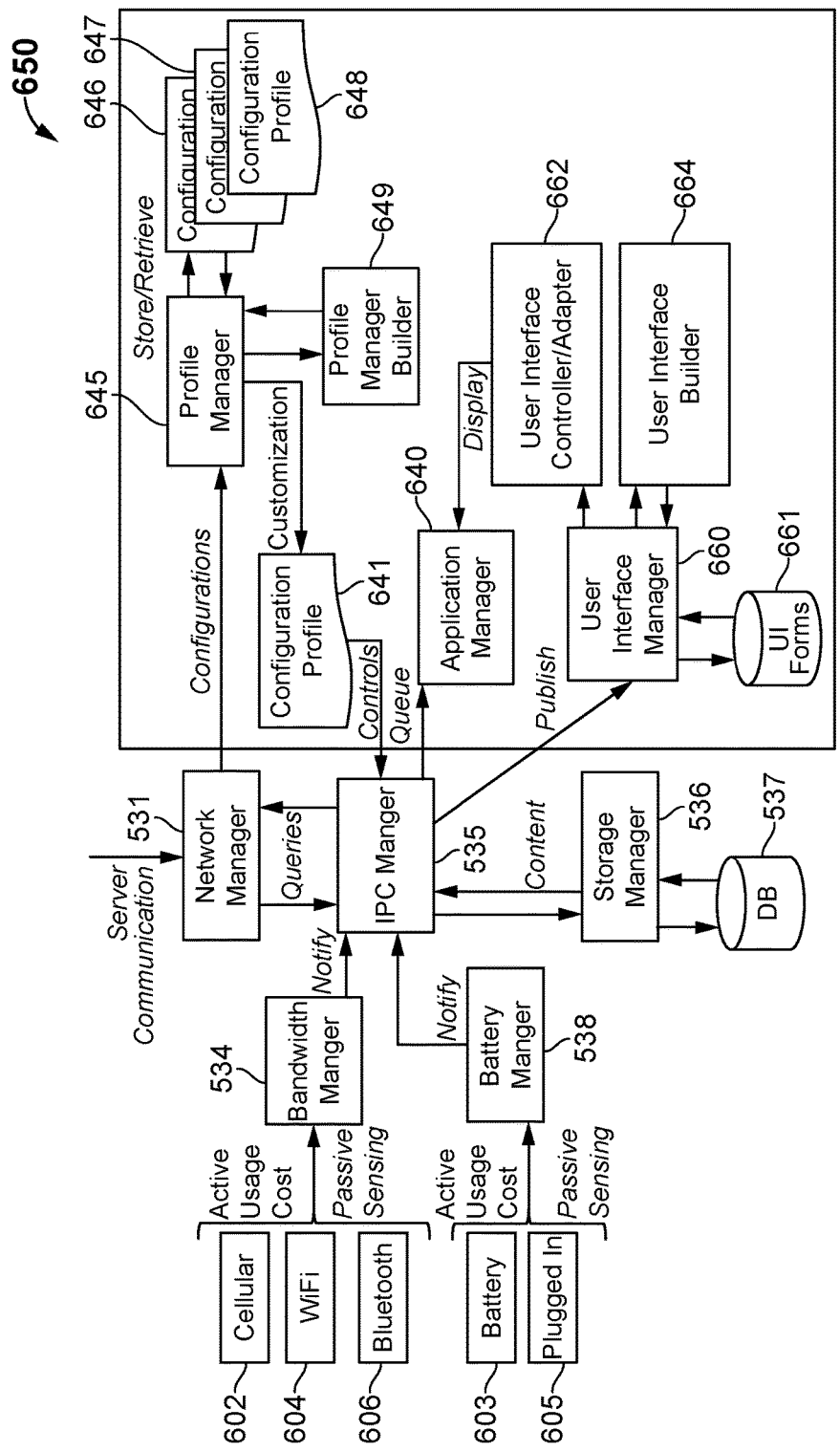
FIG. 9 depicts a system diagram of the profile manager and UI manager of the client-side system of an illustrative embodiment of the present invention.

FIG. 9 depicts an additional element of the present invention as further detailed in relation to FIG. 8 above. As seen in FIG. 9, the client side 630 includes the IPC manager 535, network manager 531, storage manager 536, battery manager 538, and bandwidth manager 534. However, in addition to the various manager components, the system also includes a profile manager 645, a profile manager builder 649, a recipient or user interface manager 660, a recipient or user interface builder 664, and a recipient or user interface controller or adapter 662. Through this enhanced system, the IPC manager 535 works with the configuration profile 641 to identify various aspects of the client device 630 and the profile of the recipient based on various aspects of interactivity of the recipient with the device and external data.

The system can use multiple configuration profiles 646, 647, 648 which are available to the profile manager 645 for use in application based on the profile manager 645 determination of the configuration profile 646, 647, 648 most likely to represent the real time personality profile for the recipient. In the event the configuration profiles 646, 647, 648 are not an appropriate profile for the determined profile of the recipient for the time that the query needs to be presented, the profile manager builder 649 can create a profile based on the known elements of a recipient profile and filling in any determined gaps to build a new configuration profile that would also then be stored and managed by the profile manager 645. Ultimately, the selected configuration profile 646, 647, 648 or a new profile built by the profile manager builder 649 will be used to determine a final configuration profile 641 which is then used by the IPC manager 535 to determine or alter the queries coming in from the network manager 531.

In addition, the system 650 includes components which help the client 630 determine an appropriate recipient or user interface from the existing recipient or user interface forms or templates from the UI Forms database 661 or to adapt (step 662) or build (step 664) a new recipient or user interface more appropriate to the real time profile of the recipient. The recipient or user interface manager 660 determines if any of the UI forms 661 are appropriate based on the profile determined by the profile manager 645. In the event the UI forms 661 are deemed insufficient, the recipient or user interface manager 660 determines if the recipient or user interface can be adapted or controlled to create a recipient or user interface appropriate for the configuration profile 641 or if a new recipient or user interface is required to be built by the recipient or user interface builder 664. Ultimately, a selected, adapted, or built recipient or user interface is presented to the application manager 640 for display on the client 630.

The recipient or user interface templates or forms used by the system for presenting queries to recipients are also based on the rules and the decision mapping engine of the system. The templates, rules, and mapping engine are downloaded to the client or device as needed during initial login and other synchronization needs during client usage. The content of these forms can also be stored locally in the local client with relevancy, personalization mapping and trending signaling occurring from the remote server with less redundancy in the sharing of the content, where the client can update when the server signals updates are available.

Requests for UI templates or forms may come from the server based on one or all of the following: Intent to send (rules or admin requested); trending/crowdsourced data, and recipient data (relevancy and personality). When the client, receives a notification from the server of an intent to send a query, the client must determine whether it has the necessary information or whether it requires more from the server. The server may provide suggestions in the notification of the profile the client should use to reduce the over the air communication time. However, the client may need a different UI form if the profile suggested is not appropriate, new or additional images are needed, or may have updated its profile. Further still, the decision making on the client may be limited based on client performance needs, storage space, networking—which may in part request more content or less when a request comes from the server. The system, including the server and client, have appropriate rules for handling and resolving the best alternative based on network limitations such as performance, bandwidth, and connectivity.

The system also makes use of a personality processing model which defines the recipient's personality to gain an understanding of what types of queries should be asked. Some individuals will respond negatively to questions or lose trust in the system if not asked in an appropriate manner. This provides a layer that can directly influence the relevancy scoring to ensure a higher degree of good quality responses for queries delivered or plan to be delivered. The enrollment for a specific personalized model could be based on varying psychology and personality mapping techniques, including OCEAN and Myers Briggs.

Continuing with FIG. 9, the IPC manager 535 also manages the profile manager 645 and the application manager 640 to control or limit some of the functionality of the profile manager 645 or recipient or user interface manager 660 based upon the bandwidth manager 534, battery manager 538 and storage manger 536. By way of example, if the battery manager 538 determines that the client 630 is low on power and profile management building through the profile manager builder 649 or recipient or user interface building through the recipient or user interface builder 664, would be too process intensive, the IPC manager 535 may instruct the profile manager 645 to limit profile selection to a profile that currently exists or may limit the recipient or user interface manager to select a UI Form 661 that already exists. Further, the IPC manager 535 through the storage manager 536 may limit the storage of a new recipient or user interface or adapted interface or may instruct the Storage Manager 536 to delete or purge seldom used data (profiles, UI Forms, and other date) in the event the database 537 is deemed to be nearing its memory capacity. Further the bandwidth manager 534 can help identify various communication paths, the reliability of such paths and the data transmission speed to determine if elements missing within any profile or recipient or user interface can be retrieved thereby allowing the IPC manager 535 to control the final configuration profile, the final displayed recipient or user interface or UI form, and the query presented to the recipient.

Figure 10:
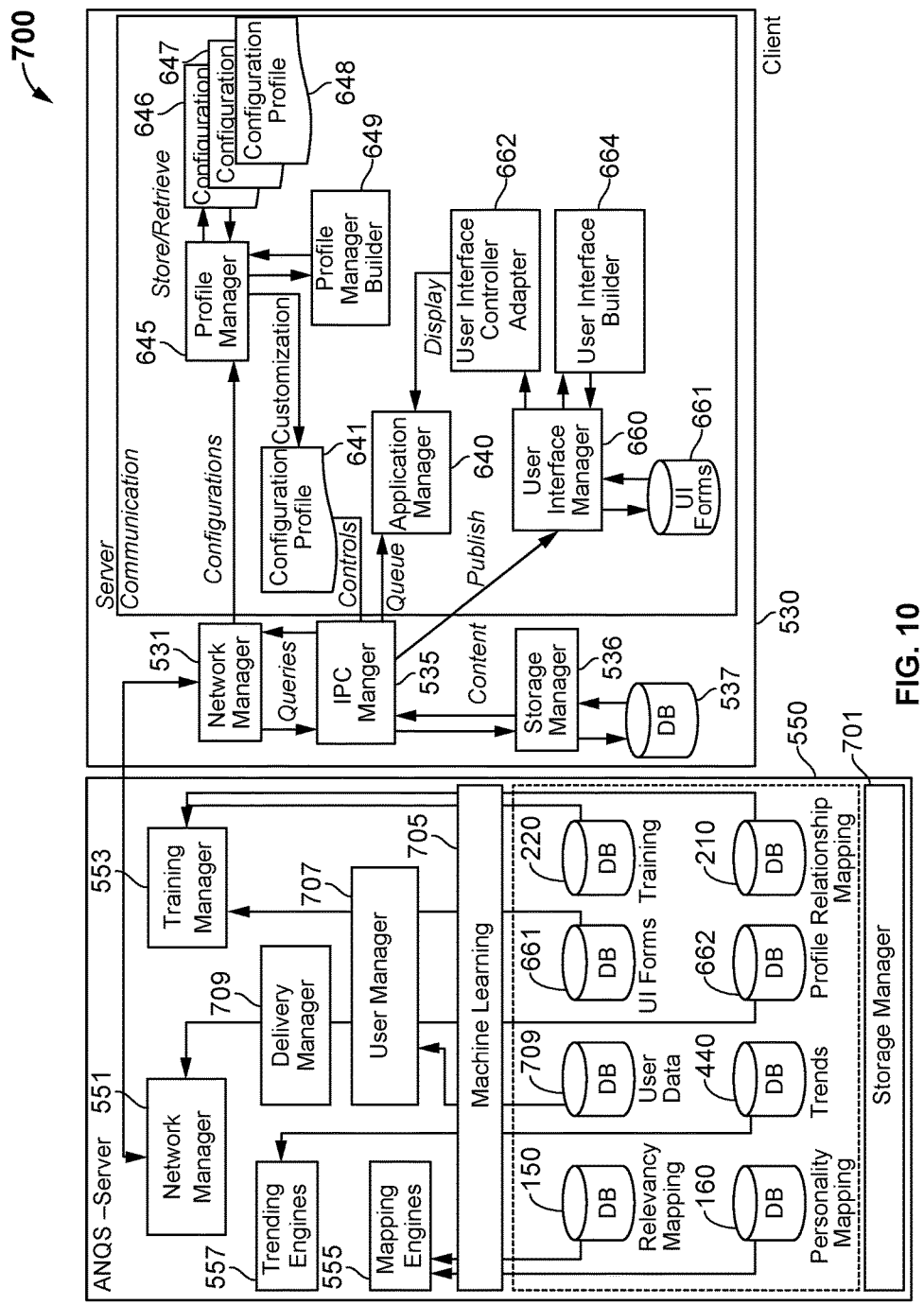
FIG. 10 depicts a system diagram of the client side and server-side manger interaction of an illustrative embodiment of the present invention.

The interaction of the client 530 and server 550 with regards to the profile manager 645 and recipient or user interface manager 660 are described in conjunction with FIG. 10. As seen in FIG. 10, the client 530 through the IPC manager 535 and the network manager 531 communicate with the server-side network manager 551. The client 530 includes the IPC manager 535, the storage manager 536, the database or memory 537, as well as, the profile manager 645, the profile manager builder 649, the application manager 640, the recipient or user interface manager 660, UI forms database 661, the recipient or user interface builder 664, and the recipient or user interface adapter or controller 662.

On the server side 550, the network manager 551 interacts with the machine learning component 705 and the numerous databases available and accessible through the system. The databases include the relevancy mapping database 150, the personality mapping database 160, the recipient database 709, the trends database 440, the UI forms database 661, the profile database 662, the training database 220, and the relationship mapping database 210. The databases and machine learning component 705 interact with the recipient manager 707 and the delivery manager 709 to present appropriate queries back to the network manager 551 for passing to the client 530. The server side 550 also interacts with the mapping engines 555, the trending engines 557 and the training manager 553 to continue to map the recipient's profile, the configurations, and the queries in combination with the various data available to the server 550 to help refine the knowledge base of the system, and the recipient profile learning on the server side 550. Through interaction of the knowledge database and machine learning 705 on the server side 550 and the logic and capabilities on the client side 530, the system is able to provide anticipated queries and recipient or user interface instructions to the client 530. The client 530 is able to make customizations in real time based upon real time profile management of the recipient and real time recipient or user interface management on the device.

Figure 11:
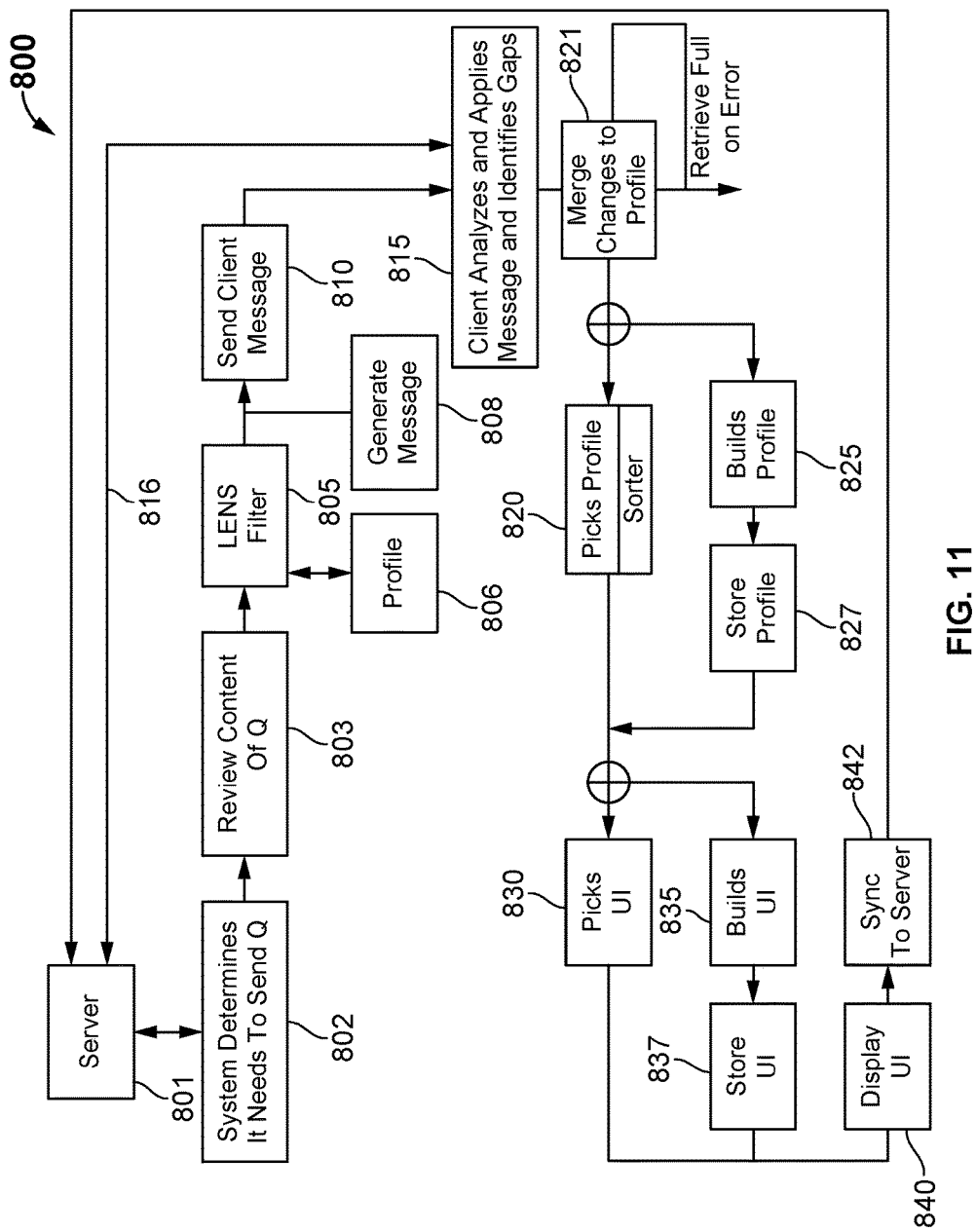
FIG. 11 depicts a flow diagram of the query messaging and client-side processing employed by the present invention.

FIG. 11 provides the flow 800 of the interaction from the server 801 to the client as it relates to the messaging provided to the client. The flow 800 is initiated by the server 801 when the system determines it needs to send a query 802 to a recipient. The system 800 reviews the contents of the query 803 and then processes the content through one or more filters 805 which includes a review of the recipient profile 806 based on the systems determined profile for the recipient at such time. When the system 800 has processed the query content, filtered and assessed it against the profile 806, it generates a message 808 which is then sent to the client 810.

The client, in step 815, receives, parses, and analyzes the message into the various components related to the server's assessment of the appropriate recipient profile and the appropriate UI. The client in step 815 also identifies any gaps within the profile data, query data, and recipient or user interface data and can respond back to the server along path 816 to fill any gaps. The analyzed message is then reviewed to determine the profile against the determination of the recipient's real time optimal profile as determined by the client device. The profile sent by the server may be a partial transmission based on the last known transmission. This partial transmission may be merged in step 821 with the client if error checking determines merge to be accurate and valid. If any errors are detected and repairs cannot be made, then the full profile file would be requested for transmission from the server. To the extent the client message includes a profile which agrees with the client-side determination then the client picks the profile in step 820 from the host of profiles available on the client. In the event the client message contains a profile which is not available on the client, the client then builds a profile in step 825, stores the profile in 827 and passes the profile along to the recipient or user interface portion of the flow. The determined profile, either built or selected, is then utilized by the system to determine an appropriate recipient or user interface along with the interface suggestions contained within the original message to the client. The system analyzes the suggested recipient or user interface from the message as well as makes any adjustments based on the determined profile and determines if a recipient or user interface exists within the system or needs to be built. If the client system determines the recipient or user interface already exists, the client will pick the appropriate UI in step 830. If the client determines the recipient or user interface does not exist within the UI forms or templates available on the client, then the client application will build a new UI in step 835, store the UI in step 837 and ultimately display the UI in step 840. The selected or built UI based on the communications from the server as well as the analysis determined related to the recipients then current profile. Ultimately, this information is synced in step 842 back the server 801 so that the server side can continue to use machine learning to further understand the recipient and to alter the database for both training and knowledge-based purposes.

In a preferred embodiment, the file transmitted in the message, whether partial or full, is structured as both filename and file content, or notation of changed content, with potentially multiple streams of compressed and uncompressed data. The filename provides an initial cue as to the existing profile relationship to the recipient. It contains flags represented as conventional letters, numbers and positions within the filename for network, battery, storage, timestamp, last transmission identifier, checksum (hash, CRC, SHA, MD5 or other method) and a simplified template guide based on personality, relevance and previous measured source data. The initial elements of the file within the message provide a quick check in comparing client and server copies and any changes therein. If there is a mismatch, then the contents in an object-notation (XML, JSON) are compared for deeper checks and merging. Each field within the file has a timestamp and related information, if the client profile file or information is out of sync with the server profile file or information, then the client will merge latest changes with the server. Only the file differences need be shared. The only condition where the file is replaced, is if the file is corrupt, then the client would replace the entire file in that case or the server would if such a case constituted the change. Within the file there is a breakdown of individualized content for varying queries classifiers. The present invention provides the ability to have a unique approach to different queries and not a single approach to one type of template or rotating template. Rather, the present invention provides a unique template which is provided or utilized based on the depth of the classification of the training DBs, the personality and the relevancy mappings.

The resulting output from the activity of the Adaptive Network Query System helps to transform queries into more appropriate messaging inclined to engage a recipient based on the recipients then current personality or state of mind.

Figure 12:
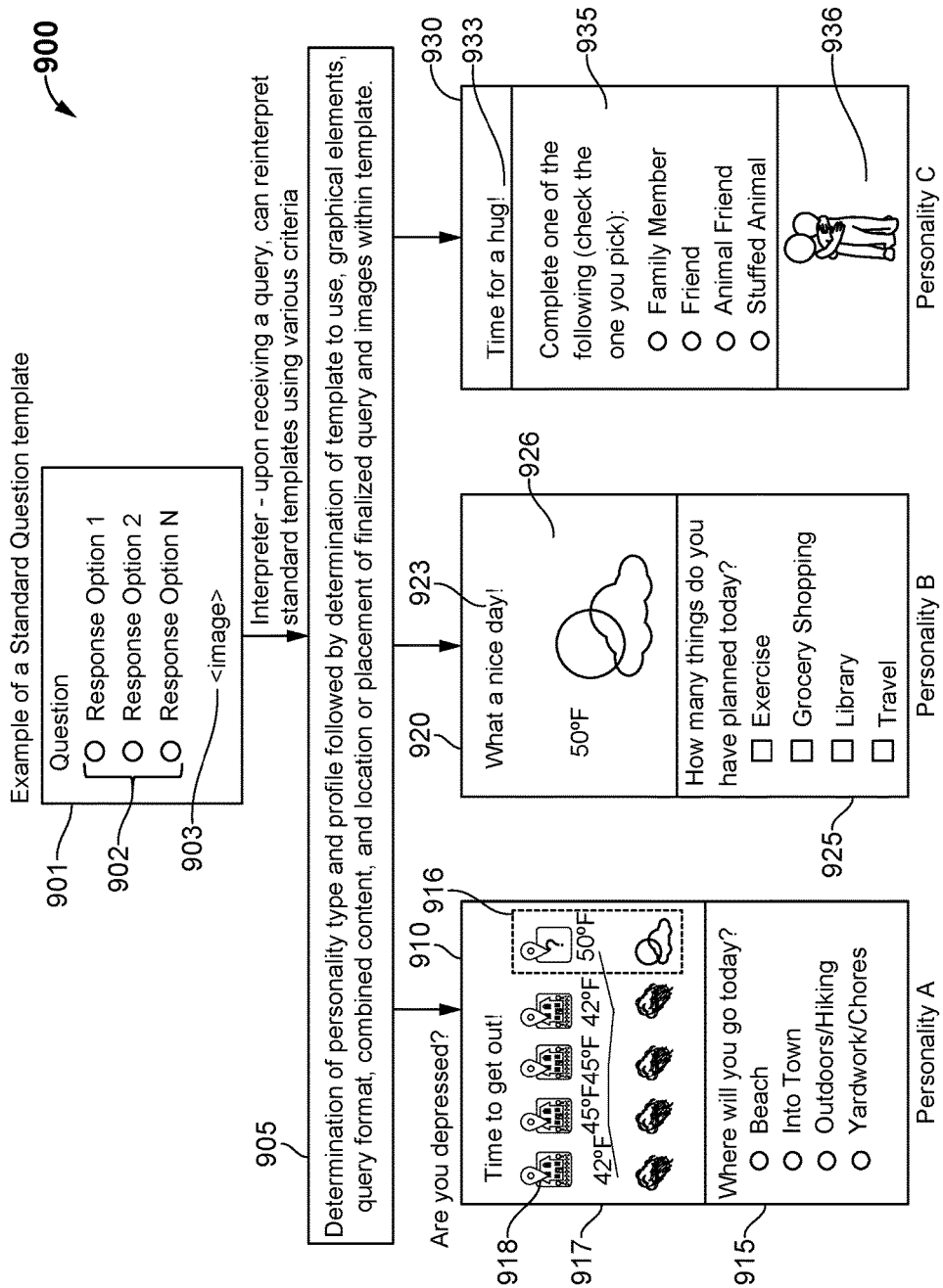
FIG. 12 depicts the user interface assembly elements of the present invention.

FIG. 12 depicts various queries in varying recipient or user interfaces and presents various examples resulting from the system of the present invention. A sample query template 901 presents a basic set of questions 902 which may include an image 903 to a recipient. However, the query 901 provides little personalization to the user let alone takes into account the recipient's then current state of mind. However, through the system, the recipient interface form or template can have varying elements which can be modified, altered or added in addition to modification of the query content and format of the content to present the recipient a far more tailored interface based on the recipient's learned and real time determined profile.

By way of an example, if the system determines that the current state of mind of the recipient, that is undergoing cancer treatment recovery, suggests a general state of depression, the system may determine and then configure the query in multiple ways. First, the recipient state of wellness would be known through measured data collection sources, and the condition of depression may be inferred by the recipient's semantic location of home, geo-location based on relative IP address or GPS, longitudinal array of past 4 days, weather patterns, and lack of interaction with device or significant interaction (i.e. limited calls or texts). On day 5 (the day a query is to be presented), if the recipient has not moved and the system determines additional scenarios which can compound, or influence (such as gloomy weather, lack of activity, poor sleep, poor diet, weight gain, water loss, increased blood pressure, increased alcohol, increased television or internet usage), then the system or device may determine the recipient is suffering depression or depression like activities. Thus, based on personality and mapping of what works best for different individuals, the recipient may see one of the query sets. The system may determine rather than asking "How are you feeling following your cancer treatment?" or even alternately "Are you depressed?" the system restates the query based on the scenario as "Time to get out!" with detail driven, and possibly live data and following question (and perhaps response) the system suggests the recipient to take action. The system may determine a single response is most appropriate to reduce time spent on the question without collecting too much from the recipient. Alternatively, the system may determine it is appropriate based on the recipient profile to provide a brief description, moderately logical, but more communication driven. Instead of asking "Are you depressed?" the system restates the query based on the scenario "What a nice day!" and following questions are purposed in a way that suggests the recipient to get involved and be active. Further, the system may not provide any description but prompts an action. Instead of asking "Are you depressed?" the system assumes some social interactions are required and restates as "Time for a hug!". The action they are to complete may be one action or one of several actions from a list and report which one they are most inclined to perform.

As seen in FIG. 12, these queries and prompts are integrated into the various sections or elements of the template. The system 900 helps transform or replace a standard query template 901 into personality profile focused templates 910, 920, 930 based on the recipients' personality type (Personality A, B, C for example) as reflected in the recipient profile stored in the system and client. For example, a standard query template 901 may have an upper element 902 and a bottom graphical element 903 for presenting queries. In contrast, a personality-based template 910, 920, 930 may present queries with an upper window 917, lower window 915 and graphical elements 916, 918. These windows 915, 917 and elements 916, 918 can be presented to the recipient in ways that provide detailed or graphical information in a readily decipherable manner. The graphics 916, 918 and the text may be selected, retrieved, or built based on the recipients then current profile.

The system of the present invention contains an Interpreter 905, which upon receiving a query can reinterpret standard templates using various criteria. The interpreter 905 processes the query and determines the personality type, profile of the recipient and then determines: the template to use; the graphical elements to use; the query format; then finalizes the combined content of the query, and determines the placement or location of the query content (images and data) to display in the selected windows of the selected template.

In the event the profile indicates the recipient has previously shown that they prefer graphical elements for longitudinal data 918 or multiple days versus specific information on the then current real time status 916, the system can present a host of information and images as seen in interface 910 or limited live imagery and data as seen in interface 920 and even more limited as seen in interface 930. In addition, the format of the question can be presented in multiple formats such as attempting to prompt the recipient where they are going as opposed to specific things that they may be planning for the day as seen in 925 or based on the profile determines the recipient needs interaction and prompts the recipient for interaction rather than specifically asking a query to get the recipient to engage the system prior to asking things about what the recipient's going to do or where the recipient's going to go as seen in section 935.

Ultimately the system can use the configuration profile of the recipient and the UI forms available or the UI builder to assemble various queries as presented in windows 915, 925, 935 within the various templates 910, 920, 930 and to present numerous graphics 916, 918, 926, 936 in a multitude of forms and formats to best engage the recipient based on the recipient's real time profile. As previously described, the queries could be content, not in the form of a question, and the system could reword or reconfigure the content (change tense, tone, argument) and determine location of the content within the templates and interface.

Insights are presented after the recipient responds to the query. The insights consist of text, graphic and data visualization content components. The end recipient learns how their answer compares with the answers of other people. Which group of other recipient s in the system that are included in the comparison, is governed by the parameters of the template. For example, the admin can configure the template to include a comparison group that includes only people with diabetes or other criteria. The Insight template also includes a short text description of a fact related to the question that helps the end recipient learn something about the topic area. Variations on the Insight template includes the responses of the specific recipient are highlighted in the visualization. In this template the "quick insight" also includes a hyperlink to a web page that includes content about the topic area. Another variation is an Insight template that includes a filter where the end recipient can select from a set of options that further filter the comparison criteria to a subset.

Figure 13:
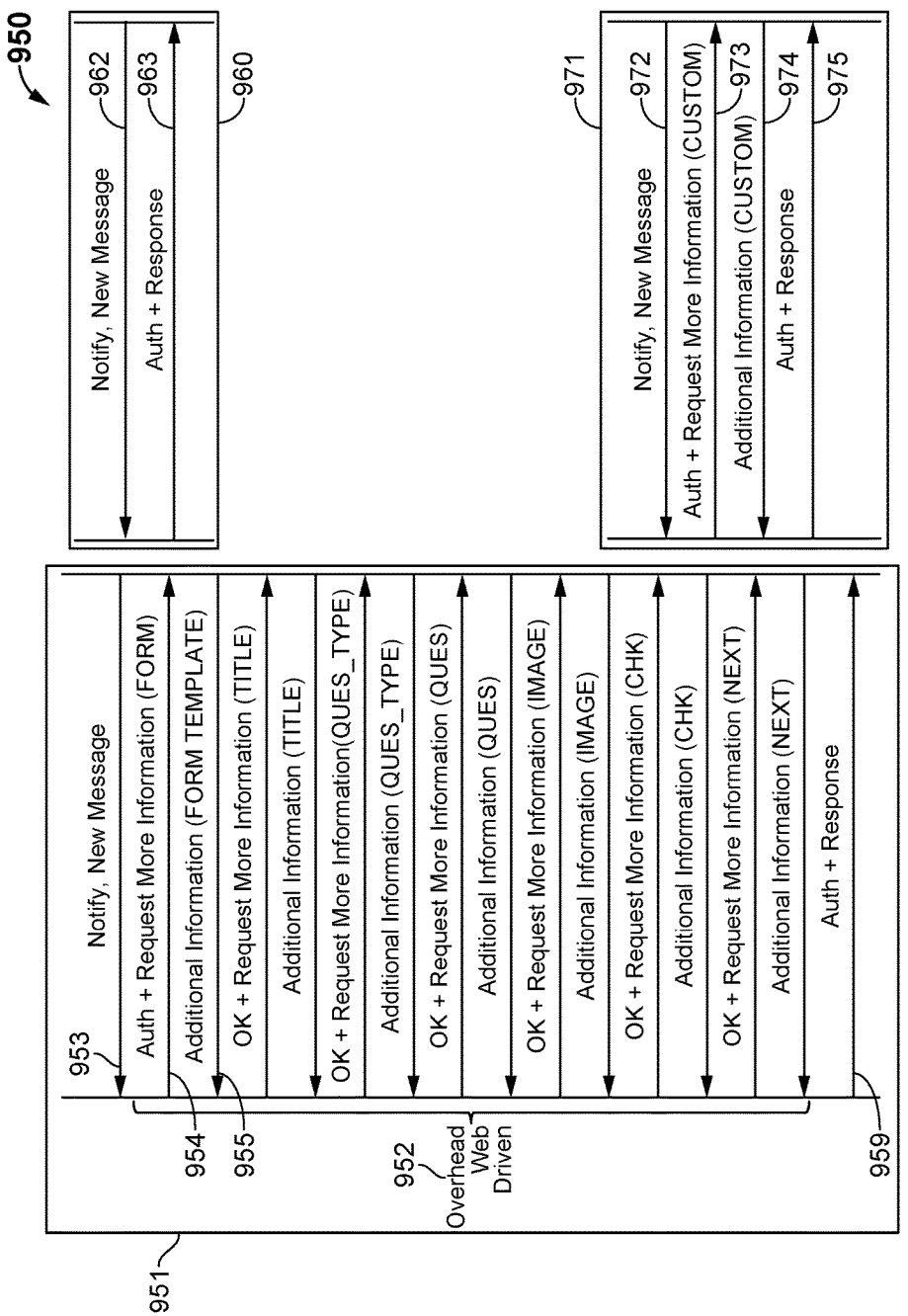
FIG. 13 depicts a flow diagram of the improved messaging of the present invention.

FIG. 13 provides a comparison 950 of the messaging of legacy systems 951 against the messaging of the current system 960 and an alternative embodiment of the present invention 971. In a known server to client messaging protocol 951, a notification 953 is sent from the server side to the client. The client then in 954 sends a message back authorizing the communication and requesting more information such information may mean it's the type of form to use. The server side then sends the additional information in step 955 back to the client in a form maybe in a form template. This process continues back and forth in what is known as an overhead web driven based messaging format 952. Ultimately through the back and forth between the client and server, a template can be transmitted, the title and queries, question types and questions and any images can be transmitted back and forth somewhat in either a multitude of messages or packet of messaging finally terminating in step 959 with the client notifying it has all of the authorization and a full response back to the server. The problem with the current messaging format 951, is that the system requires significant communications back and forth between the client and server resulting in increased bandwidth and potential issues in communication and connectivity.

The present invention provides a messaging system 960 which allows the server side to notify the client and include the new message 962 which includes the sever side's information on the query and the server side identified profile and recommended UI template. Because the client side has their own ability to now modify the profile and/or modify the UI template, the client can send a notification of the authorization and response 963 back to the server indicating the client has everything it needs. Ultimately, then the client will make determinations on does it have an appropriate profile, can it select the appropriate profile, does it need to build a new profile, does it have the appropriate UI form, does it need to build a UI form, and can it ultimately assemble the queries within a selected template with selected images, and selected or adapted query format to present the recipient with the query in a client side optimized format.

Still further, the system has the ability to make additional customizations through a secondary embodiment of a communication comparison 971 where the server sends a notification and message 972 to the client. The client then would send an authorization or request for more information 973 based upon either certain custom elements that are needed or gaps in information or gaps within the server message in communication step 973. The server in step 974 can send the additional custom information back to the client for the client to build and identify the final UI based on the final configuration profile determined by the client and send an authorization and response back to the server in communication step 975. Ultimately, the communication structure 960, 971 significantly reduces the significant number of client-to-server and server-to-client communications for repeated requests of additional information to build a template and/or structure a query in an appropriate format for the real time personality determination of the system.

In an alternative embodiment, the server may include a profile manager, a profile builder, a recipient or user interface manager, a recipient or user interface builder, and a recipient or user interface controller or adapter. The server may ping the client device to obtain the client's determination of best current configuration profile or data to determine a best current configuration profile. The server may then select, through the profile manager, a configuration profile to use. In the event the system determines the optimal current profile does not exist in the system memory, the profile builder can create or assemble a real-time profile for use.

The server profile manager then communicates the real time profile to the server-side recipient or user interface manager which determine an appropriate recipient or user interface. The recipient or user interface may come from an existing user interface form stored in memory. In the event the server recipient or user interface manager determines the stored UI forms are deemed insufficient, the server-side recipient or user interface manager determines if a stored recipient or user interface can be adapted or controlled to create a recipient appropriate UI form or if a new UI form is needed. If a new UI is needed, the user interface manager communicates with the recipient or user interface builder to build a new UI form or template based on the real-time recipient profile. The server than determines any additional modifications to the queries, wording, and graphics and transmits the information to the client. The information may include the profile, UI form, and query or may be instructions for the client to build a matching profile, UI form, for displaying the query and any related images on the display of the client device.

The systems and methods of the invention in described embodiments may be implemented as a system, method, apparatus or article of manufacture using programming and/or engineering techniques related to software, firmware, hardware, or any combination thereof. The described operations may be implemented as code maintained in a "computer readable medium", where a processor may read and execute the code from the computer readable medium. A computer readable medium may comprise media such as magnetic storage medium (e.g., hard disk drives, floppy disks, tape, etc.), optical storage (CD-ROMs, DVDs, optical disks, etc.), volatile and non-volatile memory devices (e.g., EEPROMs, ROMs, PROMs, RAMs, DRAMs, SRAMs, Flash Memory, firmware, programmable logic, etc.), etc. The code implementing the described operations may be further implemented in hardware logic (e.g., an integrated circuit chip, Programmable Gate Array (PGA), Application Specific Integrated Circuit (ASIC), etc.). Still further, the code implementing the described operations may be implemented in "transmission signals", where transmission signals may propagate through space or through a transmission media, such as an optical fiber, copper wire, etc. The transmission signals in which the code or logic is encoded may further comprise a wireless signal, satellite transmission, radio waves, infrared signals, Bluetooth, etc. The transmission signals in which the code or logic is encoded is capable of being transmitted by a transmitting station and received by a receiving station, where the code or logic encoded in the transmission signal may be decoded and stored in hardware or a computer readable medium at the receiving and transmitting stations or devices. An "article of manufacture" comprises computer readable medium, hardware logic, and/or transmission signals in which code may be implemented. A device in which the code implementing the described embodiments of operations is encoded may comprise a computer readable medium or hardware logic. Of course, those skilled in the art will recognize that many modifications may be made to this configuration without departing from the scope of the present invention, and that the article of manufacture may comprise suitable information bearing medium known in the art.

In an embodiment of the invention, the systems and methods use networks, wherein, the term, 'networks' means a system allowing interaction between two or more electronic devices, and includes any form of inter/intra enterprise environment such as the world wide web, Local Area Network (LAN), Wide Area Network (WAN), Storage Area Network (SAN) or any form of Intranet.

In an embodiment of the invention, the systems and methods can be practiced using any electronic device. An electronic device for the purpose of this invention is selected from any device capable of processing or representing data to a recipient and user and providing access to a network or any system similar to the internet, wherein the electronic device may be selected from but not limited to, personal computers, mobile phones, laptops, palmtops, tablets, portable media players and personal digital assistants.

As noted above, the processing machine used to implement the invention may be a suitable computer or other processing machine. The processing machine may also utilize (or be in the form of) any of a wide variety of other technologies including a special purpose computer, a computer system including a microcomputer, mini-computer or mainframe for example, a programmed microprocessor, a micro-controller, a peripheral integrated circuit element, a CSIC (Consumer Specific Integrated Circuit) or ASIC (Application Specific Integrated Circuit) or other integrated circuit, a logic circuit, a digital signal processor, a programmable logic device such as a FPGA, PLD, PLA or PAL, or any other device or arrangement of devices that is capable of implementing the steps of the processes of the invention.

The processing machine used to implement the invention may utilize a suitable operating system (OS). Thus, embodiments of the invention may include a processing machine running the Unix operating system, the Apple iOS operating system, the Linux operating system, the Xenix operating system, the IBM AIX™ operating system, the Hewlett-Packard UX™ operating system, the Novell Netware™ operating system, the Sun Microsystems Solaris™ operating system, the OS/2™ operating system, the BeOS™ operating system, the Macintosh operating system (such as macOS™), the Apache operating system, an OpenStep™ operating system, the Android operating system (and variations distributed by Samsung, HTC, Huawei, LG, Motorola, Google, Blackberry, among others), the Windows 10™ operating system, the Windows Phone operating system, the Windows 8™ operating system, Microsoft Windows™ Vista™ operating system, the Microsoft Windows™ XP™ operating system, the Microsoft Windows™ NT™ operating system, the Windows™ 2000 operating system, or another operating system or platform.

The systems and methods of the invention may utilize non-operating systems (aka serverless architecture) as well for distributed processing. In the processing of the invention, services on cloud computing networks leveraging systems like AWS (as offered by Amazon Web Services, Inc.), BlueMix (as offered by IBM), and Microsoft Azure, can perform data collection services using varying technologies that are spun up on demand using tools like Chef to create container based deployments like Docker, or non-container compute services (e.g. AWS Lambda).

The invention provides real-time analytics processing that requires scale on demand to the recipients and users in the system, in accordance with at least one embodiment of the invention. Such offerings as AWS lambda and Kinesis (as offered by Amazon Web Services, Inc.) are among those that may be used in implementation of the invention. For example, AWS Lambda may be utilized to execute code (to perform processes of the invention) in response to various triggers including data changes, shifts in system state, or particular action taken by recipients and users. Similarly, in an embodiment, the OS (operating system) of the invention might be encapsulated in an EC2 instance (as offered by Amazon Web Services, Inc.) or multiple instances for deployment.

It is appreciated that in order to practice the method of the invention as described above, it is not necessary that the processors and/or the memories of the processing machine be physically located in the same geographical place. That is, each of the processors and the memories used by the processing machine may be located in geographically distinct locations and connected so as to communicate in any suitable manner, such as over a network of over multiple networks. Additionally, it is appreciated that each of the processor and/or the memory may be composed of different physical pieces of equipment. Accordingly, it is not necessary that the processor be one single piece of equipment in one location and that the memory be another single piece of equipment in another location. That is, it is contemplated that the processor may be two pieces of equipment in two different physical locations. The two distinct pieces of equipment may be connected in any suitable manner. Additionally, the memory may include two or more portions of memory in two or more physical locations.

To explain further, processing as described above is performed by various components and various memories. However, it is appreciated that the processing performed by two distinct components as described above may, in accordance with a further embodiment of the invention, be performed by a single component. Further, the processing performed by one distinct component as described above may be performed by two distinct components. In a similar manner, the memory storage performed by two distinct memory portions as described above may, in accordance with a further embodiment of the invention, be performed by a single memory portion. Further, the memory storage performed by one distinct memory portion as described above may be performed by two memory portions.

Further, as also described above, various technologies may be used to provide communication between the various processors and/or memories, as well as to allow the processors and/or the memories of the invention to communicate with any other entity; i.e., so as to obtain further instructions or to access and use remote memory stores, for example. Such technologies used to provide such communication might include a network, the Internet, Intranet, Extranet, LAN, an Ethernet, or any client server system that provides communication, for example. Such communications technologies may use any suitable protocol such as TCP/IP, UDP, or OSI, for example.

Further, multiple applications may be utilized to perform the various processing of the invention. Such multiple applications may be on the same network or adjacent networks, and split between non-cloud hardware, including local (on-premises) computing systems, and cloud computing resources, for example. Further, the systems and methods of the invention may use IPC (interprocess communication) style communication for module level communication. Various known IPC mechanisms may be utilized in the processing of the invention including, for example, shared memory (in which processes are provided access to the same memory block in conjunction with creating a buffer, which is shared, for the processes to communicate with each other), data records accessible by multiple processes at one time, and message passing (that allows applications to communicate using message queues).

As described above, a set of instructions is used in the processing of the invention. The set of instructions may be in the form of a program or software. The software may be in the form of system software or application software, for example. The software might also be in the form of a collection of separate programs, a program module within a larger program, or a portion of a program module, for example. The software used might also include modular programming in the form of object oriented programming. The software tells the processing machine what to do with the data being processed.

Further, it is appreciated that the instructions or set of instructions used in the implementation and operation of the invention may be in a suitable form such that the processing machine may read the instructions. For example, the instructions that form a program may be in the form of a suitable programming language, which is converted to machine language or object code to allow the processor or processors to read the instructions. That is, written lines of programming code or source code, in a particular programming language, are converted to machine language using a compiler, assembler or interpreter. The machine language is binary coded machine instructions that are specific to a particular type of processing machine, i.e., to a particular type of computer, for example. The computer understands the machine language.

Any suitable programming language may be used in accordance with the various embodiments of the invention. Illustratively, the programming language used may include assembly language, Ada, APL, Basic, C, C++, C#, Objective C, COBOL, dBase, Forth, Fortran, Java, Modula-2, Node.JS, Pascal, Prolog, Python, REXX, Visual Basic, and/or JavaScript, for example. Further, it is not necessary that a single type of instructions or single programming language be utilized in conjunction with the operation of the system and method of the invention. Rather, any number of different programming languages may be utilized as is necessary or desirable.

Also, the instructions and/or data used in the practice of the invention may utilize any compression or encryption technique or algorithm, as may be desired. An encryption module might be used to encrypt data. Further, files or other data may be decrypted using a suitable decryption module, for example.

As described above, the invention may illustratively be embodied in the form of a processing machine, including a computer or computer system, for example, that includes at least one memory. It is to be appreciated that the set of instructions, i.e., the software for example, that enables the computer operating system to perform the operations described above may be contained on any of a wide variety of media or medium, as desired. Further, the data that is processed by the set of instructions might also be contained on any of a wide variety of media or medium. That is, the particular medium, i.e., the memory in the processing machine, utilized to hold the set of instructions and/or the data used in the invention may take on any of a variety of physical forms or transmissions, for example. Illustratively, as also described above, the medium may be in the form of paper, paper transparencies, a compact disk, a DVD, an integrated circuit, a hard disk, a floppy disk, an optical disk, a magnetic tape, a RAM, a ROM, a PROM, a EPROM, a wire, a cable, a fiber, communications channel, a satellite transmissions or other remote transmission, as well as any other medium or source of data that may be read by the processors of the invention.

Further, the memory or memories used in the processing machine that implements the invention may be in any of a wide variety of forms to allow the memory to hold instructions, data, or other information, as is desired. Thus, the memory might be in the form of a database to hold data. The database might use any desired arrangement of files such as a flat file arrangement or a relational database arrangement, for example.

In the system and method of the invention, a variety of "recipient interfaces" or "user interfaces" may be utilized to allow a recipient or user to interface with the processing machine or machines that are used to implement the invention. As used herein, a recipient or user interface includes any hardware, software, or combination of hardware and software used by the processing machine that allows a recipient or user to interact with the processing machine. A recipient or user interface may be in the form of a dialogue screen for example. A recipient or user interface may also include any of a mouse, touch screen, keyboard, voice reader, voice recognizer, dialogue screen, menu box, list, checkbox, toggle switch, a pushbutton or any other device that allows a recipient or user to receive information regarding the operation of the processing machine as it processes a set of instructions and/or provide the processing machine with information. Accordingly, the recipient or user interface is any device that provides communication between a recipient or user and a processing machine. The information provided by the recipient or user to the processing machine through the recipient or user interface may be in the form of a command, a selection of data, or some other input, for example.

As discussed above, a recipient or user interface is utilized by the processing machine that performs a set of instructions such that the processing machine processes data for a recipient or user. The recipient or user interface is typically used by the processing machine for interacting with a recipient or user either to convey information or receive information from the recipient or user. However, it should be appreciated that in accordance with some embodiments of the system and method of the invention, it is not necessary that a human recipient or user interact with a recipient or user interface used by the processing machine of the invention. Rather, it is also contemplated that the recipient or user interface of the invention might interact, i.e., convey and receive information, with another processing machine, rather than a human recipient or user. Accordingly, the other processing machine might be characterized as a recipient or user. Further, it is contemplated that a recipient or user interface utilized in the system and method of the invention may interact partially with another processing machine or processing machines, while also interacting partially with a human recipient or user.

What is claimed is:

1. A system of networked apparatuses that provide adaptive queries, the processing being performed over a network to provide communication interface amongst the networked apparatuses, each of the apparatuses in the form of a tangibly embodied computer processor, each computer processor including instructions on a non-transitory computer memory, the system comprising:
   the network over which a plurality of networked apparatuses communicate;
   an adaptive query server, the adaptive query server including:
   a query processor including instructions on a non-transitory computer medium, the non-transitory computer medium constituted by one or more data storage mediums;
   the query processor including a training manager module for loading at least one query;
   the query processor including a personality mapping module for mapping at least one recipient profile to create a recipient profile file for each individual recipient associated with the plurality of networked apparatuses, the recipient profile file stored in the one or more data storage mediums;
   the query processor including a relevancy mapping module for mapping the relevancy of the one or more queries to a plurality of individual recipients associated with the plurality of networked apparatuses;
   the query processor determining a query for a selected recipient based on the recipient profile file associated with the recipient and the relevancy mapping of the query;
   the query processor generating a query message including data on the query, the selected recipient profile, and a suggested recipient interface template; and the query processor initiating a communication including the query message to at least one recipient device associated with the selected recipient;
at least one recipient device, the recipient device including:
an adaptive processor including instructions on a non-transitory computer medium, the non-transitory computer medium constituted by one of more data storage mediums,
the adaptive processor including a profile module for determining a real time profile of the recipient associated with the recipient device and storing the profile in one of the data storage mediums on the device;
the adaptive processor processing the query message to extract the query, the selected recipient profile, and the suggested recipient interface template;
the adaptive processor comparing the selected recipient profile from the adaptive query server to the profile file on the recipient device;
the adaptive processor including a profile manager and selecting a final recipient profile from a plurality of recipient profiles stored in the one or more data storage mediums based on the comparison;
the adaptive processor including a user interface manager, the user interface manager selecting a final user interface template from a plurality of user interface templates stored in the one or more data storage mediums based on the final user profile; and
the adaptive processor generating a user interface for display on the recipient device comprised of the final user interface template, a final set of query data from the plurality of query data and selecting the location of each element of the final set of query data within the final user interface template.

2. The adaptive query network of claim 1, the query message including a file with a filename, the filename including attributes for initial profile screening by the recipient device.

3. The adaptive query network of claim 1, the query message including a file with the file including a plurality of attributes for profile screening by the recipient device.

4. The adaptive query network of claim 1, the profile module creating a new profile when the recipient's activities indicate one or more traits inconsistent with the profiles stored on the data storage mediums on the device.

5. The adaptive query network of claim 1, the user interface module creating a new user interface template when the final user profile is inconsistent with the user interface templates stored on the data storage medium of the recipient device.

6. The adaptive query network of claim 1, the adaptive processor modifying the query based on the final user profile.

7. The adaptive query network of claim 1, the query data includes images.

8. The adaptive query network of claim 1, the adaptive processor selecting images for use in the final user interface based on the final user profile.

9. The adaptive query network of claim 1, the recipient profile being a personality profile.

10. A method for dynamically adapting and displaying at least one query on a recipient device within a network of networked devices, the method comprising:
mapping, by a query processor device in communication with the recipient device, (1) a recipient profile against a set of known profiles; and (2) the relevancy of the at least one query to the recipient profile associated with the recipient device;
dynamically selecting, by the query processor, a query from the at least one query based on the recipient profile and the relevancy mapping to transmit to the recipient device;
generating, by the query processor, a query message including a plurality of query data including a plurality of attributes on the at least one query, a suggested query format, the suggested recipient profile, and a suggested user interface template;
transmitting, by the query processor device, the query message to the recipient device;
analyzing, by an adaptive processor on the recipient device, the query message and identifying the plurality of attributes;
comparing, by the adaptive processor, the plurality of attributes associated with the suggested recipient profile against a set of known profiles on the recipient device;
selecting, by the adaptive processor, a real-time recipient profile;
determining, by the adaptive processor, a final user interface template based on the suggested user interface template and the real-time recipient profile, the determining including selecting an initial user interface template from a plurality of templates on the recipient device; and
generating a user interface for display on the recipient device comprised of the final user interface template, a final set of query data from the plurality of query data and selecting the location of each element of the final set of query data within the final user interface template.

11. The method of claim 10, the method further including inserting within the query message a file.

12. The method of claim 11, the method further including generating a filename for the file, the filename including attributes for initial profile screening by the recipient device.

13. The method of claim 11, the method further including inserting a plurality of attributes within the file associated with the recipient profile and the suggested user interface template.

14. The method of claim 10, the method further including generating a new profile when the recipient's activities indicate one or more personality traits inconsistent with the at least one profile stored on the recipient device.

15. The method of claim 10, the method further including generating a new user interface template when the final user profile is inconsistent with the user interface templates stored on the recipient device.

16. The method of claim 10, the method further including modifying the query based on the final user profile.

17. The method of claim 10, the method further including selecting images for use in the final user interface from the set or query data, based on the final user profile.

18. The method of claim 10, the recipient profile being a personality profile.

19. A device for dynamically adapting and displaying at least one query, comprising;
a processor including instructions on a non-transitory computer medium, the non-transitory computer medium constituted by one or more data storage mediums;
the instructions, when executed by the processor configures the recipient device to:

receive at least one query message with a plurality of query data and analyzing the query message to identify a plurality of attributes;

compare at least one of the attributes from the plurality of attributes from the query message with a set of user profiles stored in the one or more storage mediums on the device;

select a real-time user profile;

determine a final user interface template based on the real-time user profile, the determining including analyzing a plurality of templates stored in the one or more data storage mediums using the selected real-time user profile and then selecting the final user interface template; and generating a user interface for display on the device comprised of the final user interface template, a final set of query data from the plurality of query data; and selecting the location of each element of the final set of query data within the final user interface template.

20. The device of claim 19, the query message including a file with a filename, the filename including attributes for initial profile screening by the recipient device.

21. The device of claim 19, the query message including a file with the file including a plurality of attributes for profile screening by the recipient device.

22. The device of claim 19, the profile module creating a new profile when the recipient's activities indicate one or more traits inconsistent with the profiles stored on the data storage mediums on the device.

23. The device of claim 19, the adaptive processor modifying the query based on the selected real-time user profile.

24. The device of claim 19, the real-time user profile being a personality profile.

* * * * *

UNITED STATES PATENT AND TRADEMARK OFFICE
CERTIFICATE OF CORRECTION

PATENT NO. : 10,095,688 B1  
APPLICATION NO. : 15/943309  
DATED : October 9, 2018  
INVENTOR(S) : Schilling et al.

Page 1 of 1

It is certified that error appears in the above-identified patent and that said Letters Patent is hereby corrected as shown below:

In the Claims

In Claim 1, Column 31, Line 30, insert -- (i) -- before generating a user, thereof.
In Claim 1, Column 31, Line 32, delete "," and insert -- and --, thereof.
In Claim 1, Column 31, Line 33, delete "the" and insert -- a --, thereof.
In Claim 1, Column 31, Line 33, insert -- (ii) -- before selecting, delete "the" and insert -- a --, thereof.

In Claim 5, Column 31, Line 49, delete "module" and insert -- manager --, thereof.

In Claim 10, Column 32, Line 19, delete "suggested", thereof.
In Claim 10, Column 32, Line 31, delete "," and insert -- and --, thereof.
In Claim 10, Column 32, Line 33, after selecting delete "the" and insert -- a --, thereof.

In Claim 19 Column 32, Line 67, delete "recipient", thereof.
In Claim 19, Column 33, Line 2, delete "analyzing" and insert -- analyze --, thereof.
In Claim 19, Column 33, Line 15, delete "generating" and insert -- generate --, thereof.
In Claim 19, Column 33, Line 16, delete "," and insert -- and --, thereof.
In Claim 19, Column 34, Line 1, delete "selecting the" and insert -- select a --, thereof.

In Claim 20, Column 34, Line 5, delete "recipient", thereof.

In Claim 21, Column 34, Line 8, delete "recipient", thereof.

Signed and Sealed this
Twentieth Day of October, 2020

Andrei Iancu
*Director of the United States Patent and Trademark Office*